US011331380B2

(12) United States Patent
Xu

(10) Patent No.: US 11,331,380 B2
(45) Date of Patent: May 17, 2022

(54) CEREBLON-BASED HETERODIMERIZABLE CHIMERIC ANTIGEN RECEPTORS

(71) Applicant: CELGENE CORPORATION, Summit, NJ (US)

(72) Inventor: Shuichan Xu, San Diego, CA (US)

(73) Assignee: CELGENE CORPORATION, Summit, NJ (US)

( * ) Notice: Subject to any disclaimer, the term of this patent is extended or adjusted under 35 U.S.C. 154(b) by 477 days.

(21) Appl. No.: 16/343,375

(22) PCT Filed: Oct. 19, 2017

(86) PCT No.: PCT/US2017/057474
§ 371 (c)(1),
(2) Date: Apr. 18, 2019

(87) PCT Pub. No.: WO2018/075820
PCT Pub. Date: Apr. 26, 2018

(65) Prior Publication Data
US 2019/0240304 A1  Aug. 8, 2019

Related U.S. Application Data

(60) Provisional application No. 62/410,822, filed on Oct. 20, 2016.

(51) Int. Cl.
| *A61K 39/00* | (2006.01) |
| *A61P 35/00* | (2006.01) |
| *A61K 39/395* | (2006.01) |
| *A61K 31/454* | (2006.01) |
| *A61K 45/06* | (2006.01) |
| *A61K 31/7088* | (2006.01) |
| *C07K 14/47* | (2006.01) |
| *C07K 14/705* | (2006.01) |
| *C07K 16/28* | (2006.01) |
| *C07K 16/30* | (2006.01) |
| *C07K 16/32* | (2006.01) |

(52) U.S. Cl.
CPC ........ *A61K 39/0011* (2013.01); *A61K 31/454* (2013.01); *A61K 31/7088* (2013.01); *A61K 39/395* (2013.01); *A61K 45/06* (2013.01); *A61P 35/00* (2018.01); *C07K 14/4702* (2013.01); *C07K 14/70521* (2013.01); *C07K 16/2878* (2013.01); *C07K 16/3069* (2013.01); *C07K 16/32* (2013.01); *A61K 2039/5156* (2013.01); *C07K 2319/03* (2013.01)

(58) Field of Classification Search
CPC ................................................. A61K 39/0011
See application file for complete search history.

(56) References Cited

U.S. PATENT DOCUMENTS

| 5,665,577 A | 9/1997 | Sodroski et al. |
| 5,677,171 A | 10/1997 | Hudziak et al. |
| 5,686,281 A | 11/1997 | Roberts |
| 5,712,149 A | 1/1998 | Roberts |
| 5,720,937 A | 2/1998 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,783,404 A | 7/1998 | Koski |
| 5,843,728 A | 12/1998 | Seed et al. |
| 5,906,936 A | 5/1999 | Eshhar et al. |
| 5,948,893 A | 9/1999 | June et al. |
| 5,994,136 A | 11/1999 | Naldini et al. |
| 6,103,521 A | 8/2000 | Capon et al. |
| 6,165,464 A | 12/2000 | Hudziak et al. |
| 6,165,782 A | 12/2000 | Naldini et al. |
| 6,319,494 B1 | 11/2001 | Capon et al. |
| 6,352,694 B1 | 3/2002 | June et al. |
| 6,387,371 B1 | 5/2002 | Hudziak et al. |
| 6,399,063 B1 | 6/2002 | Hudziak et al. |
| 6,410,319 B1 | 6/2002 | Raubitschek et al. |
| 6,428,953 B1 | 8/2002 | Naldini et al. |
| 6,534,055 B1 | 3/2003 | June et al. |
| 6,692,964 B1 | 2/2004 | June et al. |
| 6,756,036 B2 | 6/2004 | Reiter et al. |
| 6,790,939 B2 | 9/2004 | Reiter et al. |
| 6,825,326 B2 | 11/2004 | Reiter et al. |
| 6,887,466 B2 | 5/2005 | June et al. |
| 6,905,681 B1 | 6/2005 | June et al. |
| 7,052,906 B1 | 5/2006 | Lawson et al. |
| 7,070,995 B2 | 7/2006 | Jensen |
| 7,083,981 B2 | 8/2006 | Naldini et al. |
| 7,250,299 B1 | 7/2007 | Naldini et al. |
| 7,265,209 B2 | 9/2007 | Jensen |
| 7,344,715 B2 | 3/2008 | Raison et al. |

(Continued)

FOREIGN PATENT DOCUMENTS

| EP | 2582722 A4 | 4/2013 |
| WO | WO 1996005309 A2 | 2/1996 |

(Continued)

OTHER PUBLICATIONS

Camicia et al. (Molecular Cancer, Dec. 11, 2015 (Dec. 11, 2015), vol. 14:207, pp. 1-62.). (Year: 2015).*
Camicia et al., 2015, "Novel drug targets for personalized precision medicine in relapsed/refractory diffuse large B-cell lymphoma: a comprehensive review," Mol. Cancer, 14:207, pp. 1-62.
Carpenito et al., 2009, "Control of large, established tumor xenografts with genetically retargeted human T cells containing CD28 and CD137 domains," Proc Natl Acad Sci USA, 106(9):3360-3365.

(Continued)

*Primary Examiner* — Scott Long
(74) *Attorney, Agent, or Firm* — Morrison & Foerster LLP

(57) ABSTRACT

Provided herein are modified T lymphocytes comprising chimeric receptors and methods thereof.

22 Claims, 1 Drawing Sheet

(56) References Cited

U.S. PATENT DOCUMENTS

| | | | |
|---|---|---|---|
| 7,407,656 B2 | 8/2008 | Reiter et al. |
| 7,446,179 B2 | 11/2008 | Jensen et al. |
| 7,446,190 B2 | 11/2008 | Sadelain et al. |
| 7,446,191 B2 | 11/2008 | Jensen |
| 7,462,352 B2 | 12/2008 | Hansen et al. |
| 7,485,296 B2 | 2/2009 | Reiter et al. |
| 7,514,537 B2 | 4/2009 | Jensen |
| 7,527,786 B2 | 5/2009 | Reiter et al. |
| 7,541,442 B2 | 6/2009 | Gudas et al. |
| 7,556,803 B2 | 7/2009 | Raison et al. |
| 7,595,379 B2 | 9/2009 | Gudas et al. |
| 7,655,461 B2 | 2/2010 | Finn et al. |
| 7,662,378 B2 | 2/2010 | Goldenberg et al. |
| 7,736,644 B2 | 6/2010 | Weber et al. |
| 7,741,465 B1 | 6/2010 | Eshhar et al. |
| 7,902,338 B2 | 3/2011 | Hansen et al. |
| 7,919,090 B2 | 4/2011 | Goldenberg et al. |
| 7,951,369 B2 | 5/2011 | Goldenberg et al. |
| 8,062,636 B2 | 11/2011 | Goldenberg et al. |
| 8,088,908 B2 | 1/2012 | Sherman et al. |
| 8,147,831 B2 | 4/2012 | Hansen et al. |
| 8,211,422 B2 | 7/2012 | Eshhar et al. |
| 8,216,572 B2 | 7/2012 | Goldenberg et al. |
| 8,287,865 B2 | 10/2012 | Hansen et al. |
| 8,324,353 B2 | 12/2012 | Jensen |
| 8,399,645 B2 | 3/2013 | Campana et al. |
| 8,404,817 B2 | 3/2013 | Sherman et al. |
| 8,444,973 B2 | 5/2013 | Tedder et al. |
| 8,465,743 B2 | 6/2013 | Rosenberg et al. |
| 8,497,118 B2 | 7/2013 | Jensen |
| 8,822,647 B2 | 9/2014 | Jensen |
| 9,469,684 B2 | 10/2016 | Finn et al. |
| 10,150,816 B2 | 12/2018 | Abbott et al. |
| 2005/0118185 A1 | 6/2005 | Hombach et al. |
| 2008/0102027 A1 | 5/2008 | Dunn et al. |
| 2009/0081172 A1 | 3/2009 | Finn et al. |
| 2009/0155282 A1 | 6/2009 | Weber et al. |
| 2009/0156790 A1 | 6/2009 | Weber et al. |
| 2010/0105136 A1 | 4/2010 | Carter et al. |
| 2010/0135974 A1 | 6/2010 | Eshhar et al. |
| 2010/0215651 A1 | 8/2010 | Blein et al. |
| 2012/0148552 A1 | 6/2012 | Jensen |
| 2012/0321667 A1 | 12/2012 | Sentman |
| 2013/0084294 A1 | 4/2013 | Tedder et al. |
| 2013/0289261 A1 | 10/2013 | Finn et al. |
| 2014/0162282 A1 | 6/2014 | Schafer et al. |
| 2015/0291562 A1 | 10/2015 | Crew et al. |
| 2016/0151465 A1 | 6/2016 | Slawin et al. |
| 2016/0264665 A1* | 9/2016 | Lim .................. C07K 16/30 |

FOREIGN PATENT DOCUMENTS

| | | |
|---|---|---|
| WO | WO 2011160119 A2 | 12/2011 |
| WO | WO 2011160119 A3 | 12/2011 |
| WO | WO 2011160119 A8 | 12/2011 |
| WO | WO 2012033885 A1 | 3/2012 |
| WO | WO 2012050374 A2 | 4/2012 |
| WO | WO 2012058460 A2 | 5/2012 |
| WO | WO 2012058460 A3 | 5/2012 |
| WO | WO 2012079000 A1 | 6/2012 |
| WO | WO 2012079000 A4 | 6/2012 |
| WO | WO 2012099973 A2 | 7/2012 |
| WO | WO 2012099973 A3 | 7/2012 |
| WO | WO 2012129514 A1 | 9/2012 |
| WO | WO 2012138475 A1 | 10/2012 |
| WO | WO 2012138858 A1 | 10/2012 |
| WO | WO 2013040557 A2 | 3/2013 |
| WO | WO 2013040557 A3 | 3/2013 |
| WO | WO 2013059593 A1 | 4/2013 |
| WO | WO 2013063419 A2 | 5/2013 |
| WO | WO 2013063419 A3 | 5/2013 |
| WO | WO 2013067492 A1 | 5/2013 |
| WO | WO 2013070468 A1 | 5/2013 |
| WO | WO 2014100385 A1 | 6/2014 |
| WO | WO 2014124143 A1 | 8/2014 |
| WO | WO 2015127351 A1 | 8/2015 |
| WO | WO 2016025454 A2 | 2/2016 |
| WO | WO 2016025454 A3 | 2/2016 |

OTHER PUBLICATIONS

Gandhi et al., 2014, "Immunomodulatory agents lenalidomide and pomalidomide co-stimulate T cells by inducing degradation of T cell repressors Ikaros and Aiolos via modulation of the E3 ubiquitin ligase complex CRL4$^{CRBN}$," Br. J. Haematol., 164(6):811-821.

GenBank Gene ID: 10320, IKZF1 Ikaros family zinc finger 1 [*Homo sapiens* (human)], updated Aug. 6, 2019, retreived from https://www.ncbi.nlm.nih.gov/gene/10320 on Aug. 9, 2019.

GenBank Gene ID: 22806, IKZF3 Ikaros family zinc finger 3 [*Homo sapiens* (human)], updated Aug. 4, 2019, retreived from https://www.ncbi.nlm.nih.gov/gene/22806 on Aug. 9, 2019.

GenBank Gene ID: 51185, CRBN cereblon [*Homo sapiens* (human)], updated Jun. 17, 2019, retreived from https://www.ncbi.nlm.nih.gov/gene/51185 on Aug. 9, 2019.

Hyrup et al., 1996, "Peptide nucleic acids (PNA): synthesis, properties and potential applications," Bioorg. Med. Chem., 4(1):5-23.

International Search Report and Written Opinion of International Patent Application PCT/US2017/057474 (Pub No. WO 2018075820) dated Jan. 22, 2018 (19 pages).

Kocoglu et al., 2016, "The Role of Immunotherapy in Multiple Myeloma," Pharmaceuticals (Basel), 9(1):1-13.

Siraathof et al., 2005, "An inducible caspase 9 safety switch for T-cell therapy," Blood, 105(11):4247-4254.

Summerton et al., 1997, "Morpholino antisense oligomers: design, preparation, and properties," Antisense & Nucleic Acid Drug Dev., 7(3):187-195.

UniProtKB—Q03267 (IKZF1_Mouse), DNA-binding protein Ikaros, retrieved from https://www.uniprot.org/uniprot/Q03267-1 on Aug. 9, 2019, Integrated into UniProtKB/Swiss-Prot on Oct. 1, 1993, Last sequence update Dec. 15, 1998.

UniProtKB—Q96SW2 (CRBN_Human), Protein cereblon, retrieved from https://www.uniprot.org/uniprot/Q96SW2 on Aug. 9, 2019, Integrated into UniProtKB/Swiss-Prot on Aug. 30, 2005, Last sequence update Dec. 1, 2001.

UniProtKB—Q9UKT9 (IKZF3_Human), Zinc finger protein Aiolos, retrieved from https://www.uniprot.org/uniprot/Q9UKT9 on Aug. 9, 2019, Integrated into UniProtKB/Swiss-Prot on Sep. 19, 2002, Last sequence update Nov. 4, 2008.

Wu et al., 2015, "Remote control of therapeutic T cells through a small molecule-gated chimeric receptor," Science, 350(6258):aab4077 (11 pages).

\* cited by examiner

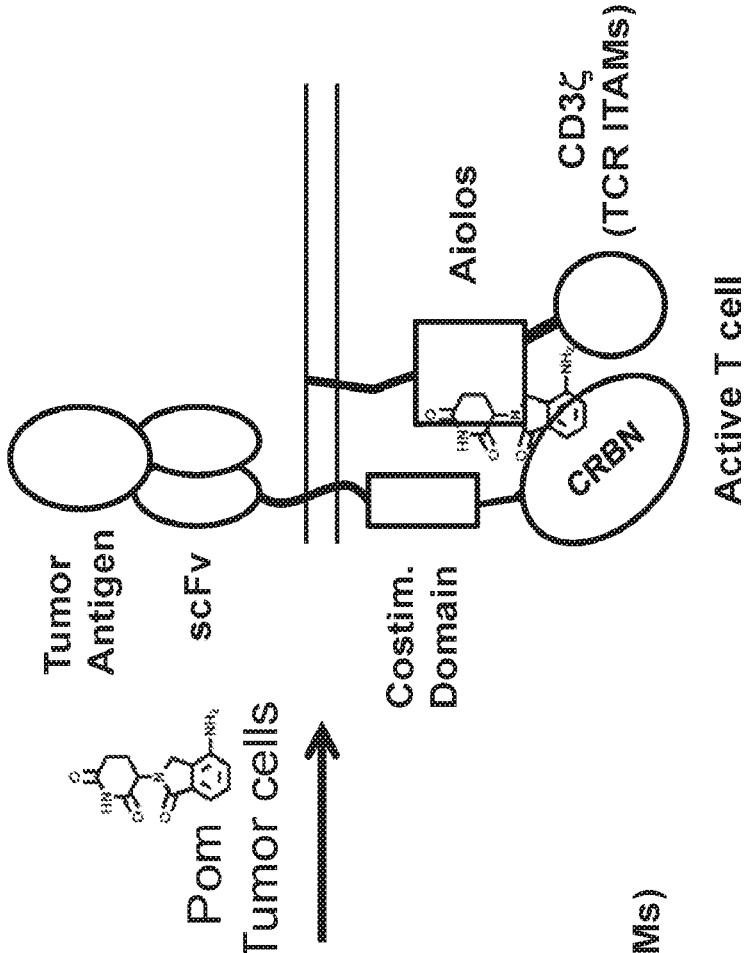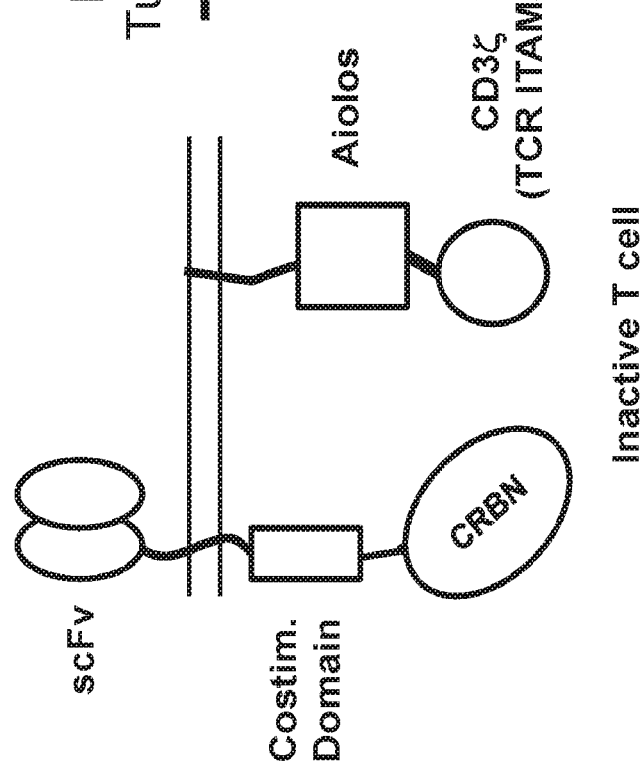

CEREBLON-BASED HETERODIMERIZABLE CHIMERIC ANTIGEN RECEPTORS

This application is a U.S. National Stage Application of International Patent Application No. PCT/US2017/057474, filed Oct. 19, 2017, which claims the benefit of U.S. Provisional Patent Application No. 62/410,822, filed Oct. 20, 2016, which is incorporated by reference herein in its entirety.

1. FIELD

The disclosure herein relates to the field of immunology, and more specifically, to the modification of T lymphocytes or other immune cells.

2. BACKGROUND

Cells of the immune system such as T lymphocytes (also referred to as T cells) recognize and interact with specific antigens through receptors or receptor complexes which, upon recognition or an interaction with such antigens, cause activation of the cell. An example of such a receptor is the antigen-specific T lymphocyte receptor complex (TCR/CD3), a complex of eight proteins. The T cell receptor (TCR) is expressed on the surface of T lymphocytes. One component, CD3, which has an invariant structure, is responsible for intracellular signaling following occupancy of the TCR by ligand. The T lymphocyte receptor for antigen-CD3 complex (TCR/CD3) recognizes antigenic peptides that are presented to it by the proteins of the major histocompatibility complex (MHC). Complexes of MHC and peptide are expressed on the surface of antigen presenting cells and other T lymphocyte targets. Stimulation of the TCR/CD3 complex results in activation of the T lymphocyte and a consequent antigen-specific immune response. The TCR/CD3 complex plays a central role in the effector function and regulation of the immune system.

T lymphocytes require a second, costimulatory signal to become fully active. Without such a signal, T lymphocytes are either non-responsive to antigen binding to the TCR, or become anergic. Such a costimulatory signal, for example, is provided by CD28, a T lymphocyte protein, which interacts with CD80 and CD86 on antigen-producing cells. ICOS (Inducible COStimulator), another T lymphocyte protein, provides a costimulatory signal when bound to ICOS ligand.

Chimeric antigen receptors (CARs) are polypeptides genetically engineered to contain essential antigen-binding, signaling and stimulatory functions of the TCR complex. T lymphocytes bearing such CARs are generally referred to as CAR-T cells or CAR-T lymphocytes. However, while CARs can effectively target T lymphocytes to specific tumor-associated or tumor-specific antigens, normal, healthy cells that also express such antigens also can be targeted. Described herein are modified chimeric receptors that overcome this shortcoming of current CAR design.

3. SUMMARY

In one aspect, provided herein are Chimeric Antigen Receptors (CARs) comprising (a) a first polypeptide comprising cereblon or a functional portion thereof and (b) a second polypeptide comprising a cereblon-associated protein or a functional portion thereof, wherein the first polypeptide or the second polypeptide, or both polypeptides, comprise additional components of CARs, such as an antigen-binding domain, a transmembrane domain, a cell signaling domain, and/or a costimulatory domain. When the first and second polypeptides of the CARs are expressed together in an immune cell (e.g., in a T lymphocyte) in the presence of a cereblon-binding compound, (e.g., as described herein), the cereblon (or functional portion thereof, e.g., as described herein) of the first polypeptide and cereblon-associated protein (or functional portion thereof, e.g., as described herein) of the second polypeptide bind the cereblon-binding compound resulting in formation of a heterodimer with CAR function. Thus, activity of the CARs described herein (e.g., in vivo activity) can be selectively controlled by contacting a cell expressing the first and second polypeptides of the CARs (e.g., T lymphocytes engineered to express said CARs) with a cereblon-binding compound. When the CAR, expressed in an immune cell, is contacted with a cereblon-binding compound, and the CAR binds to an antigen, e.g., a tumor-associated antigen or tumor-specific antigen, the CAR transmits both primary and costimulatory signals, thereby activating the immune cell.

In a specific embodiment, provided herein is a CAR comprising (a) a first polypeptide comprising an antigen-binding domain, a transmembrane domain, and cereblon or a functional portion thereof, wherein said cereblon (or functional portion thereof) is capable of binding to a cereblon-binding compound; and (b) a second polypeptide comprising a transmembrane domain, cereblon-associated protein or a functional portion thereof, wherein said cereblon-associated protein (or functional portion thereof) is capable of binding a cereblon-binding compound, and a primary cell signaling domain; wherein in the presence of said cereblon-binding compound, said first polypeptide and said second polypeptide form a heterodimer. In a specific embodiment, the cereblon-associated protein is Aiolos or Ikaros. In another specific embodiment, the first polypeptide comprises a costimulatory domain. In another specific embodiment, the second polypeptide comprises a costimulatory domain. In another specific embodiment, the first polypeptide and the second polypeptide comprise a costimulatory domain. In another specific embodiment, the first polypeptide comprises a costimulatory domain and the second polypeptide does not comprise a costimulatory domain. In another specific embodiment, the second polypeptide comprises a costimulatory domain and the first polypeptide does not comprise a costimulatory domain. In another specific embodiment, said cereblon-binding compound is pomalidomide (4-amino-2-[(3RS)-(2,6-dioxopiperidin-3-yl)-1H-isoindole-1,3(2H)-dione). In another specific embodiment, said cereblon-binding compound is thalidomide ((RS)-2-(2,6-dioxopiperidin-3-yl)-1H-isoindole-1,3 (2H)-dione). In another specific embodiment, said cereblon-binding compound is lenalidomide (3-(4-amino-1-oxo-1,3-dihydro-2H-isoindol-2-yl)piperidine-2,6-dione). In another specific embodiment, said cereblon-binding compound is 3-[4-(4-morpholin-4-ylmethyl-benzyloxy)-1-oxo-1,3-dihydro-Isoindol-2-yl]-piperidine-2,6-dione. In another specific embodiment, said cereblon-binding compound is 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, a transmembrane domain, and cereblon or a functional portion thereof, and (b) a second polypeptide comprising, in order from N-terminus to C-terminus, a transmembrane domain, a cereblon-associated protein or a functional portion thereof, and a primary T cell signaling domain. In a specific embodiment, the cereblon-associated protein is Aiolos or Ikaros. In another specific embodiment, the first polypeptide comprises a costimulatory domain. In another specific embodiment, the second polypeptide comprises a costimulatory domain. In another specific embodiment, the first polypeptide and the second polypeptide comprise a costimulatory domain. In another specific embodiment, the first polypeptide comprises a costimulatory domain and the second polypeptide does not comprise a costimulatory domain. In another specific embodiment, the second polypeptide comprises a costimulatory domain and the first polypeptide does not comprise a costimulatory domain. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, cereblon or a functional portion thereof, and a transmembrane domain, and (b) a second polypeptide comprising, in order from N-terminus to C-terminus, a cereblon-associated protein or a functional portion thereof, a transmembrane domain, and a primary T cell signaling domain. In a specific embodiment, the cereblon-associated protein is Aiolos or Ikaros. In another specific embodiment, the first polypeptide comprises a costimulatory domain. In another specific embodiment, the second polypeptide comprises a costimulatory domain. In another specific embodiment, the first polypeptide and the second polypeptide comprise a costimulatory domain. In another specific embodiment, the first polypeptide comprises a costimulatory domain and the second polypeptide does not comprise a costimulatory domain. In another specific embodiment, the second polypeptide comprises a costimulatory domain and the first polypeptide does not comprise a costimulatory domain. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising an antigen-binding domain, a transmembrane domain, and a cereblon-associated protein or a functional portion thereof, wherein said cereblon-associated protein (or functional portion thereof) is capable of binding to a cereblon-binding compound; and (b) a second polypeptide comprising a transmembrane domain, cereblon or a functional portion thereof, wherein said cereblon (or functional portion thereof) is capable of binding a cereblon-binding compound, and a primary cell signaling domain; wherein in the presence of said cereblon-binding compound, said first polypeptide and said second polypeptide form a heterodimer. In a specific embodiment, the cereblon-associated protein is Aiolos or Ikaros. In a specific embodiment, the first polypeptide comprises a costimulatory domain. In another specific embodiment, the second polypeptide comprises a costimulatory domain. In another specific embodiment, the first polypeptide and the second polypeptide comprise a costimulatory domain. In another specific embodiment, the first polypeptide comprises a costimulatory domain and the second polypeptide does not comprise a costimulatory domain. In another specific embodiment, the second polypeptide comprises a costimulatory domain and the first polypeptide does not comprise a costimulatory domain. In a specific embodiment, said cereblon-binding compound is pomalidomide (4-amino-2-[(3RS)-(2,6-dioxopiperidin-3-yl)-1H-isoindole-1,3(2H)-dione). In another specific embodiment, said cereblon-binding compound is thalidomide ((RS)-2-(2,6-dioxopiperidin-3-yl)-1H-isoindole-1,3(2H)-dione). In another specific embodiment, said cereblon-binding compound is lenalidomide (3-(4-amino-1-oxo-1,3-dihydro-2H-isoindol-2-yl)piperidine-2,6-dione). In another specific embodiment, said cereblon-binding compound is 3-[4-(4-morpholin-4-ylmethyl-benzyloxy)-1-oxo-1,3-dihydro-Isoindol-2-yl]-piperidine-2,6-dione. In another specific embodiment, said cereblon-binding compound is 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, a transmembrane domain, and cereblon-associated protein or a functional portion thereof, and (b) a second polypeptide comprising, in order from N-terminus to C-terminus, a transmembrane domain, cereblon or a functional portion thereof, and a primary T cell signaling domain. In a specific embodiment, the cereblon-associated protein is Aiolos or Ikaros. In a specific embodiment, the first polypeptide comprises a costimulatory domain. In another specific embodiment, the second polypeptide comprises a costimulatory domain. In another specific embodiment, the first polypeptide and the second polypeptide comprise a costimulatory domain. In another specific embodiment, the first polypeptide comprises a costimulatory domain and the second polypeptide does not comprise a costimulatory domain. In another specific embodiment, the second polypeptide comprises a costimulatory domain and the first polypeptide does not comprise a costimulatory domain. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, a cereblon-associated protein or a functional portion thereof, and a transmembrane domain, and (b) a second polypeptide comprising, in order from N-terminus to C-terminus, cereblon or a functional portion thereof, a transmembrane domain, and a primary T cell signaling domain. In a specific embodiment, the cereblon-associated protein is Aiolos or Ikaros. In another specific embodiment, the first polypeptide comprises a costimulatory domain. In another specific embodiment, the second polypeptide comprises a costimulatory domain. In another specific embodiment, the first polypeptide and the second polypeptide comprise a costimulatory domain. In another specific embodiment, the first polypeptide comprises a costimulatory domain and the second polypeptide does not comprise a costimulatory domain.

In another specific embodiment, the second polypeptide comprises a costimulatory domain and the first polypeptide does not comprise a costimulatory domain. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, a transmembrane domain, cereblon or a functional portion thereof, and a primary cell signaling domain, and (b) a second polypeptide comprising, in order from N-terminus to C-terminus, a transmembrane domain, a cereblon-associated protein or a functional portion thereof, and a costimulatory domain. In a specific embodiment, the cereblon-associated protein is Aiolos or Ikaros. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, cereblon or a functional portion thereof, a transmembrane domain, and a polypeptide comprising a primary cell signaling domain, and (b) a second polypeptide comprising, in order from N-terminus to C-terminus, a cereblon-associated protein or a functional portion thereof, a transmembrane domain, and a costimulatory domain. In a specific embodiment, the cereblon-associated protein is Aiolos or Ikaros. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, a transmembrane domain, a cereblon-associated protein or a functional portion thereof, and a primary cell signaling domain, and (b) a second polypeptide comprising, in order from N-terminus to C-terminus, a transmembrane domain, cereblon or a functional portion thereof, and a costimulatory domain. In a specific embodiment, the cereblon-associated protein is Aiolos or Ikaros. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, a cereblon-associated protein or a functional portion thereof, a transmembrane domain, and a polypeptide comprising a primary cell signaling domain, and (b) a second polypeptide comprising, in order from N-terminus to C-terminus, cereblon or a functional portion thereof, a transmembrane domain, and a costimulatory domain. In a specific embodiment, the cereblon-associated protein is Aiolos or Ikaros. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In certain embodiments, when the first or second polypeptide of a CAR described herein comprises a primary cell signaling domain, said polypeptide is CD3ζ. In a specific embodiment, said cell signaling domain is human.

In certain embodiments, when the first or second polypeptide of a CAR described herein comprises a primary cell signaling domain, said primary cell signaling domain is or comprises an immunoreceptor tyrosine-based activation motif (ITAM) primary cell signaling domain. In a specific embodiment, said ITAM is derived from one or more of the following: FcRγ, FcRβ, CD3ζ, CD3γ, CD3δ, CD3ε, CD5, CD22, CD20, CD79a, CD79b, CD278 (ICOS), FcεRI, CD66d, DAP10, and/or DAP12. In a specific embodiment, said cell signaling domain is human.

In certain embodiments, when the first and/or second polypeptide of a CAR described herein comprises a costimulatory domain, the costimulatory domain is derived from one or more of the following: CD28, 4-1BB (CD137), OX40, an activating NK cell receptor, BTLA, a Toll ligand receptor, CD2, CD7, CD27, CD30, CD40, CDS, ICAM-L LFA-1 (CD11a/CD18), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8α, CD8β, IL2Rβ, IL2Rγ, IL7Rα, ITGA4, VLA1, CD49a, ITGA4, IA4, CD49D, ITGA6, VLA-6, CD49f, ITGAD, CD1 d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, DAP10, DAP12, a ligand of CD83, an MHC class I molecule, a TNF receptor protein, an immunoglobulin-like protein, a cytokine receptor, an integrin, and/or a signaling lymphocytic activation molecule. In a specific embodiment, said costimulatory domain is human.

In certain embodiments, the transmembrane domain of the first polypeptide and/or second polypeptide of the CARs provided herein comprises the transmembrane domain from: the alpha chain of the T-cell receptor, the beta chain of the T-cell receptor, the zeta chain of the T-cell receptor, CD28, CD3ε, CD45, CD4, CD5, CD8, CD9, CD16, CD22, CD33, CD37, CD64, CD80, CD86, CD134, CD137, or CD154. In a specific embodiment, said transmembrane domain is human.

In certain embodiments, the antigen-binding domain of a CAR described herein comprises a receptor.

In certain embodiments, the antigen-binding domain of a CAR described herein comprises an antibody, or binding fragment thereof. In a specific embodiment, the binding fragment of said antibody is a single chain Fv fragment (scFv).

In certain embodiments, the antigen bound by an antigen-binding domain of a CAR described herein is an antigen on a tumor cell. In a specific embodiment, said antigen is an antigen of a solid tumor cell. In another specific embodiment, said antigen is an antigen of a blood cancer cell.

In another specific embodiment, the antigen bound by an antigen-binding domain of a CAR described herein is a tumor-associated antigen (TAA) or a tumor-specific antigen (TSA). In a specific embodiment, the TAA or TSA is one or more of the following, or a fragment thereof: 4-1BB, 5T4, 8H9, B7-H6, adenocarcinoma antigen, α-fetoprotein, B Cell Maturation Antigen (BCMA), BAFF, B-lymphoma cell, C242 antigen, CA9, carcinoembryonic antigen, CA-125, carbonic anhydrase 9 (CA-IX), CCR4, CD3, CD4, CD19, CD20, CD22, CD23 (IgE receptor), CD28, CD30 (TNFRSF8), CD33, CD38, CD40, CD44v6, CD44v7/8, CD51, CD52, CD56, CD74, CD80, CD123, CD152, CD171, CD200, CD221, CE7, CEA, C-MET, CNT0888, CTLA-4, DR5, EpCAM, ErbB2, ErbB3/4, EGFR, EGFRvIII, EphA2, EGP2, EGP40, FAP, Fetal AchR, fibronectin extra domain-B, folate receptor-a, folate receptor 1, G250/CAIX, GD2, GD3, glycoprotein 75, GPNMB, HER2/neu, HGF, HLA-AI MAGE A1, HLA-A2 NY-ESO-1, HMW-MAA, human scatter factor receptor kinase, IGF-1 receptor, IGF-I, IgGl, IL-6, IL-13, IL-13 receptor a2, IL-11 receptor a, insulin-like growth factor I receptor, integrin a5I31, integrin avI33, Kappa light chain, L1-CAM, Lambda light chain, Lewis Y, mesothelin, MORAb-009, MS4A1, MUC1, MUC16, mucin CanAg, NCAM, N-glycolylneuraminic acid, NKG2D ligands, NPC-1C, PDGF-R a, PDL192, phosphatidylserine, prostate-specific cancer antigen (PSCA), prostatic carcinoma cells, PSMA, PSC1, RANKL, RON, ROR1, SCH 900105, SDC1, SLAMF7, sp17, TAG72, tenascin C, TGF β2, TGF-I3, TL1A, TRAIL-R1, TRAIL-R2, tumor antigen CTAA16.88, VEGF-A, VEGF receptors, VEGFR-1, VEGFR2, TEM1, TEM8, and/or vimentin.

In another aspect, provided herein are nucleic acids encoding the CARs described herein, i.e., nucleic acids encoding the first polypeptide and nucleic acids encoding the second polypeptide of the CARs described herein. In certain embodiments, a first polypeptide of a CAR described herein is encoded by a first nucleic acid (polynucleotide) and the second polypeptide of a CAR described herein is encoded by a second nucleic acid (polynucleotide). In a specific embodiment, provided herein is a nucleic acid (polynucleotide) that encodes both the first polypeptide and second polypeptide of a CAR described herein.

In certain embodiments, the CAR polypeptide-encoding nucleic acids described herein are comprised within a nucleic acid vector. In a specific embodiment, said vector is a retroviral vector. In another specific embodiment, said vector is a lentiviral vector.

In certain embodiments, the CAR polypeptide-encoding nucleic acids described herein are operably linked to a promoter. In a specific embodiment, said promoter is a T cell-specific promoter, a natural killer (NK) cell-specific promoter, an inducible promoter that functions within T cells or NK cells, or a constitutive promoter.

In another aspect, provided herein are cells (referred to herein as "CAR cells") comprising the CAR-encoding nucleic acids and/or vectors described herein. Said cells include prokaryotic (e.g., bacterial) cells and eukaryotic (e.g., mammalian) cells. In a specific embodiment provided herein is a T cell, e.g., a CD4+, a CD+ T cell, a T effector cell, or a T memory cell, comprising a CAR described herein. In another specific embodiment provided herein is a natural killer cell comprising a CAR described herein.

The CAR cells provided herein, e.g., T cells comprising a CAR-encoding nucleic acid(s) described herein or expressing a CAR described herein (i.e., expressing the first and second polypeptide of a CAR described herein) can be activated when contacted with (i) the antigen to which the CAR is specific (that is, the antigen recognized by the antigen-binding domain of the CAR) and (ii) a cereblon-binding compound. Accordingly, in another aspect, provided herein are methods for activating a cell (e.g., a T cell or NK cell) that comprises and/or expresses a CAR described herein, said methods comprising contacting the cell with an antigen that binds the CAR's antigen-binding domain and further contacting the cell with a cereblon-binding compound. In a specific embodiment, said cell is contacted with said antigen and said cereblon-binding compound in vivo, i.e., contact occurs following administration of the cell to a subject. In another specific embodiment, said cell is administered to a subject and given a specified period of time to locate and come into contact with the antigen to which the CAR is specific, followed by administration of a cereblon-binding compound to the subject.

In certain embodiments, the CAR cells provided herein further comprise an artificial cell death polypeptide comprising an apoptosis-inducing domain and a dimerization domain, wherein the artificial cell death polypeptide is dimerizable using a dimerizing agent, and wherein when the artificial cell death polypeptide is dimerized, the polypeptide generates an apoptosis-inducing signal in said cell. In a specific embodiment, said dimerizing agent is rapamycin or an analog of rapamycin (rapalog). In another specific embodiment, said dimerizing agent is AP1903 (rimiducid). In another specific embodiment, said dimerizing agent is not a cereblon-binding compound. In a specific embodiment, said dimerization domain is FK binding domain or an analog thereof. In another specific embodiment, said dimerizing agent is an antibody that binds to said FK binding domain.

In another aspect, provided herein are methods for killing target cells that express an antigen bound by the antigen-binding domain of a CAR described herein, wherein said methods comprise (i) contacting said target cells with a cell (e.g., a T cell or NK cell) comprising/expressing a CAR described herein and (ii) contacting said CAR-expressing cell with a cereblon-binding compound, wherein in the presence of said antigen and said cereblon-binding compound the CAR-expressing cell becomes activated. In a specific embodiment, said target cell is a cancer cell, e.g., a blood cancer cell or a solid tumor cell. In another specific embodiment, said target cell expresses one or more the following antigens, or an antigenic fragment thereof: 4-1BB, 5T4, 8H9, B7-H6, adenocarcinoma antigen, α-fetoprotein, B Cell Maturation Antigen (BCMA), BAFF, B-lymphoma cell, C242 antigen, CA9, carcinoembryonic antigen, CA-125, carbonic anhydrase 9 (CA-IX), CCR4, CD3, CD4, CD19, CD20, CD22, CD23 (IgE receptor), CD28, CD30 (TNFRSF8), CD33, CD38, CD40, CD44v6, CD44v7/8, CD51, CD52, CD56, CD74, CD80, CD123, CD152, CD171, CD200, CD221, CE7, CEA, C-MET, CNT0888, CTLA-4, DRS, EpCAM, ErbB2, ErbB3/4, EGFR, EGFRvIII, EphA2, EGP2, EGP40, FAP, Fetal AchR, fibronectin extra domain-B, folate receptor-a, folate receptor 1, G250/CAIX, GD2, GD3, glycoprotein 75, GPNMB, HER2/neu, HGF, HLA-AI MAGE A1, HLA-A2 NY-ESO-1, HMW-MAA, human scatter factor receptor kinase, IGF-1 receptor, IGF-I, IgGl, IL-6, IL-13, IL-13 receptor a2, IL-11 receptor a, insulin-like growth factor I receptor, integrin a5131, integrin avI33, Kappa light chain, L1-CAM, Lambda light chain, Lewis Y, mesothelin, MORAb-009, MS4A1, MUC1, MUC16, mucin CanAg, NCAM, N-glycolylneuraminic acid, NKG2D ligands, NPC-1C, PDGF-R a, PDL192, phosphatidylserine, prostate-specific cancer antigen (PSCA), prostatic carcinoma cells, PSMA, PSC1, RANKL, RON, ROR1, SCH 900105, SDC1, SLAMF7, sp17, TAG72, tenascin C, TGF β 2, TGF-I3, TL1A, TRAIL-R1, TRAIL-R2, tumor antigen CTAA16.88, VEGF-A, VEGF receptors, VEGFR-1, VEGFR2, TEM1, TEM8, and/or vimentin.

In another aspect, provided herein are methods of treating cancer, said methods comprising (i) administration of a population of CAR cells described herein, e.g., a T cells or NK cells, that comprise/express a CAR described herein (e.g., comprise a CAR-encoding nucleic acid(s) described herein or express a CAR described herein), wherein said CAR comprises an antigen-binding domain specific for a cancer antigen (e.g., TSA or TAA) to a subject (for example, a human subject) and (ii) administering to the subject a composition comprising cereblon-binding compound. In a specific embodiment, said population of cells is administered first to the subject, followed by administration of the composition comprising a cereblon-binding compound at a specified period of time after administration of the cell population, e.g., 30 minutes, 1 hour, 6 hours, 12 hours, 1 day, 2 days, 3 days, 4 days, 5 days, 6 days, or 1 week after administration of the cell population. In a specific embodiment, said antigen bound by said CAR is 4-1BB, 5T4, 8H9, B7-H6, adenocarcinoma antigen, α-fetoprotein, B Cell Maturation Antigen (BCMA), BAFF, B-lymphoma cell, C242 antigen, CA9, carcinoembryonic antigen, CA-125, carbonic anhydrase 9 (CA-IX), CCR4, CD3, CD4, CD19, CD20, CD22, CD23 (IgE receptor), CD28, CD30 (TNFRSF8), CD33, CD38, CD40, CD44v6, CD44v7/8, CD51, CD52, CD56, CD74, CD80, CD123, CD152, CD171, CD200, CD221, CE7, CEA, C-MET, CNT0888, CTLA-4, DRS, EpCAM, ErbB2, ErbB3/4, EGFR, EGFRvIII, EphA2, EGP2, EGP40, FAP, Fetal AchR, fibronectin extra domain-B, folate receptor-a, folate receptor 1, G250/CAIX, GD2, GD3, glycoprotein 75, GPNMB, HER2/neu, HGF, HLA-AI MAGE A1, HLA-A2 NY-ESO-1, HMW-MAA, human scatter factor receptor kinase, IGF-1 receptor, IGF-I, IgGl, IL-6, IL-13, IL-13 receptor a2, IL-11 receptor a, insulin-like growth factor I receptor, integrin a5I31, integrin avI33, Kappa light chain, L1-CAM, Lambda light chain, Lewis Y, mesothelin, MORAb-009, MS4A1, MUC1, MUC16, mucin CanAg, NCAM, N-glycolylneuraminic acid, NKG2D ligands, NPC-1C, PDGF-R a, PDL192, phosphatidylserine, prostate-specific cancer antigen (PSCA), prostatic carcinoma cells, PSMA, PSC1, RANKL, RON, ROR1, SCH 900105, SDC1, SLAMF7, sp17, TAG72, tenascin C, TGF β2, TGF-I3, TL1A, TRAIL-R1, TRAIL-R2, tumor antigen CTAA16.88, VEGF-A, VEGF receptors, VEGFR-1, VEGFR2, TEM1, TEM8, and/or vimentin.

In a specific embodiment, the cereblon-binding compound administered to a subject in accordance with the methods of treating cancer described herein is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl) piperidine-2,6-dione.

A non-limiting list of cancers that can be treated in accordance with the methods of treatment described herein includes lymphoma, leukemia, lung cancer, breast cancer, prostate cancer, adrenocortical carcinoma, thyroid carcinoma, nasopharyngeal carcinoma, melanoma, skin carcinoma, colorectal carcinoma, desmoid tumor, aesmoplastic small round cell tumor, endocrine tumor, Ewing sarcoma, peripheral primitive neuroectodermal tumor, solid germ cell tumor, hepatoblastoma, neuroblastoma, non-rhabdomyosarcoma soft tissue sarcoma, osteosarcoma, retinoblastoma, rhabdomyosarcoma, Wilms tumor, glioma, glioblastoma, myxoma, fibroma, and lipoma. Exemplary lymphomas and leukemias include, without limitation, chronic lymphocytic leukemia (small lymphocytic lymphoma), B-cell prolymphocytic leukemia, lymphoplasmacytic lymphoma, Waldenstrom macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma.

In another aspect, provided herein is a dimerizable artificial cell death receptor comprising (a) a first polypeptide comprising an apoptosis-inducing domain (or functional portion thereof) and cereblon (or functional portion thereof) and (b) a second polypeptide comprising an apoptosis-inducing domain (or functional portion thereof) and Aiolos (or a functional portion thereof), wherein said cereblon (or functional portion thereof) and said Aiolos (or functional portion thereof) are both capable of binding a cereblon-binding compound, and wherein said first polypeptide and said second polypeptide dimerize in the presence of said cereblon-binding compound to generate an apoptosis-inducing signal. In a specific embodiment, said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In a specific embodiment, provided herein is a dimerizable artificial cell death receptor comprising (a) a first polypeptide comprising a transmembrane protein that comprises a transmembrane domain and an intracellular domain comprising an apoptosis-inducing domain (or functional portion thereof) and cereblon (or functional portion thereof); and (b) a second polypeptide comprising an apoptosis-inducing domain (or functional portion thereof) and a cereblon-associated protein (or functional portion thereof). In a specific embodiment, said second polypeptide comprises a transmembrane protein comprising a transmembrane domain and an intracellular domain comprising an apoptosis-inducing domain (or functional portion thereof) and a cereblon-associated protein (or functional portion thereof). In a specific embodiment, said cereblon-associated protein is Aiolos or Ikaros.

In another specific embodiment, provided herein is a dimerizable artificial cell death receptor comprising (a) a first polypeptide comprising a transmembrane protein that comprises an extracellular domain comprising cereblon (or functional portion thereof), a transmembrane domain, and an intracellular domain comprising an apoptosis-inducing domain (or functional portion thereof); and (b) a second polypeptide comprising an apoptosis-inducing domain (or functional portion thereof) and a cereblon-associated protein (or functional portion thereof). In another specific embodiment, said second polypeptide comprises a transmembrane protein comprising a transmembrane domain and an intracellular domain comprising an apoptosis-inducing domain (or functional portion thereof) and a cereblon-associated protein (or functional portion thereof). In another specific embodiment, said second polypeptide comprises a transmembrane protein that comprises an extracellular domain comprising a cereblon-associated protein (or functional portion thereof), a transmembrane domain, and an intracellular domain comprising an apoptosis-inducing domain (or functional portion thereof). In a specific embodiment, the cereblon-associated protein is Aiolos or Ikaros.

In another specific embodiment, provided herein is a dimerizable artificial cell death receptor comprising (a) a first polypeptide comprising a transmembrane protein that comprises an apoptosis-inducing domain (or functional portion thereof) and cereblon (or functional portion thereof); and (b) a second polypeptide comprising a transmembrane protein that comprises a transmembrane domain and an intracellular domain comprising an apoptosis-inducing domain (or functional portion thereof) and a cereblon-associated protein (or functional portion thereof). In a specific embodiment, the cereblon-associated protein is Aiolos or Ikaros.

In another specific embodiment, provided herein is a dimerizable artificial cell death receptor comprising (a) a first polypeptide comprising a transmembrane protein that comprises an apoptosis-inducing domain (or functional portion thereof) and cereblon (or functional portion thereof); and (b) a second polypeptide comprising a transmembrane protein that comprises an extracellular domain comprising a cereblon-associated protein (or functional portion thereof), a transmembrane domain, and an intracellular domain comprising an apoptosis-inducing domain (or functional portion thereof). In a specific embodiment, the cereblon-associated protein is Aiolos or Ikaros.

In certain embodiments, the apoptosis-inducing domain of the dimerizable artificial cell death receptors provided herein is a caspase. In a specific embodiment, said caspase is caspase 9, caspase 8, or caspase 3.

In another aspect, provided herein are nucleic acids encoding the dimerizable artificial cell death receptors described herein, i.e., nucleic acids encoding the first polypeptide and nucleic acids encoding the second polypeptide of the dimerizable artificial cell death receptors described herein. In certain embodiments, a first polypeptide of a dimerizable artificial cell death receptors described herein is encoded by a first nucleic acid (polynucleotide) and the second polypeptide of a dimerizable artificial cell death receptors described herein is encoded by a second nucleic acid (polynucleotide). In a specific embodiment, provided herein is a nucleic acid (polynucleotide) that encodes both the first polypeptide and second polypeptide of a dimerizable artificial cell death receptor described herein.

In certain embodiments, the dimerizable artificial cell death receptor-encoding nucleic acids described herein are comprised within a nucleic acid vector. In a specific embodiment, said vector is a retroviral vector. In another specific embodiment, said vector is a lentivirial vector.

In certain embodiments, the dimerizable artificial cell death receptor-encoding nucleic acids described herein are operably linked to a promoter. In a specific embodiment, said promoter is a T cell-specific promoter, a natural killer (NK) cell-specific promoter, an inducible promoter that functions within T cells or NK cells, or a constitutive promoter.

In another aspect, provided herein are cells (referred to herein as "cell death receptor cells") comprising the dimerizable artificial cell death receptor-encoding nucleic acids described herein and/or vectors described herein. Said cells include prokaryotic (e.g., bacterial) cells and eukaryotic (e.g., mammalian) cells. In a specific embodiment provided herein is a T cell, e.g., a CD4+, a CD8+ T cell, a T effector cell, or a T memory cell, comprising a dimerizable artificial cell death receptor described herein. In another specific embodiment provided herein is a natural killer cell comprising a dimerizable artificial cell death receptor described herein.

The cell death receptor cells provided herein, e.g., T cells or NK cells comprising a dimerizable artificial cell death receptor-encoding nucleic acid(s) described herein or expressing a dimerizable artificial cell death receptor described herein (i.e., expressing the first and second polypeptide of a dimerizable artificial cell death receptor described herein) can be induced to undergo apoptosis when contacted with a cereblon-binding compound, e.g., when contacted with pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In certain embodiments, the cell death receptor cells provided herein further comprise a CAR, for example, a first-generation CAR, a second-generation CAR, or a third-generation CAR. In a specific embodiment, said CAR comprises two or more extracellular antigen-targeting domains. In another specific embodiment, said CAR comprises an extracellular domain that binds to an interleukin that is a negative regulator of T cell activity, and an intracellular domain from an interleukin receptor that is a positive regulator of T cell activity. In another specific embodiment, apoptosis is induced in a cell comprising an artificial cell death receptor and a CAR by contacting the cell with a cereblon-binding compound, e.g., pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

3.1. BRIEF DESCRIPTION OF THE DRAWINGS

FIG. 1: Use of a cereblon-binding compound (e.g., pomalidomide) to regulate CAR T cell activity. Shown is a schematic representation of a split CAR on a T cell (with a first polypeptide comprising a tumor-antigen-binding domain, a costimulatory domain such as CD28, and cereblon, and a second polypeptide comprising an ITAM such as CD3ζ and a cereblon-associated protein such as Aiolos) that is activated upon exposure to pomalidomide and tumor antigen, wherein pomalidomide regulates CAR activity by inducing dimerization of the split CAR. CRBN: cereblon; POM: pomalidomide; Costim. Domain: costimulatory Domain.

4. DETAILED DESCRIPTION

On-target but off-tumor effects mediated by therapeutic immune cells expresing CARs, which potentially lead to toxicity, can be reduced or eliminated by expressing in such cells modulatable CARs that require both a primary and costimulatory signal for activation. This separation, as disclosed herein, is accomplished through the use of CARs comprising two artificial polypeptides, wherein (i) the first polypeptide comprises cereblon (or functional portion thereof) and the second polypeptide comprises a cereblon-associated protein (or functional portion thereof), (ii) the components of the CAR required for activation are divided across the two polypeptides, and (iii) the CAR is activated in the presence of a cereblon-binding compound that binds cereblon and the cereblon-associated protein.

CAR-mediated on-target, off-tumor effects also can be reduced or eliminated by the use dimerizable artificial cell death receptors, which allow for on demand killing of cells expressing such receptors. Such dimerizable artificial cell death receptors, as described herein, comprise a first polypeptide comprising an apoptosis-inducing domain and a dimerization domain, e.g., cereblon (or functional portion thereof) and a second polypeptide comprising an apoptosis-inducing domain and a complementary dimerization domain, e.g., a cereblon-associated protein (or functional portion thereof). Cells expressing such dimerizable artificial cell death receptors can be induced to undergo apoptosis by contacting them with a cereblon-binding compound capable of dimerizing the first and second polypeptides and thus activating the apoptosis-inducing domain.

4.1. Chimeric Antigen Receptors and Uses Thereof 4.1.1. Chimeric Antigen Receptor Constructs Provided herein are Chimeric Antigen Receptors (CARs) comprising (a) a first polypeptide comprising cereblon or a functional portion thereof and (b) a second polypeptide comprising a cereblon-associated protein or a functional portion thereof, wherein the first polypeptide or the second polypeptide, or both polypeptides, comprise remaining components of CARs, such as an antigen-binding domain, a transmembrane domain, a cell signaling domain, and/or a costimulatory domain. When the first and second polypeptides of the CARs are expressed together in an immune cell (e.g., in a T lymphocyte or natural killer cell) in the presence of a cereblon-binding compound, cereblon (or functional portion thereof) of the first polypeptide and said cereblon-associated protein (or functional portion thereof) of the second polypeptide bind the cereblon-binding compound resulting in formation of a heterodimer with CAR function. Thus, activity of the CARs described herein (e.g., in vivo activity) can be selectively controlled by contacting a cell expressing the first and second polypeptides of the CARs (e.g., T lymphocytes engineered to express said CARs) with a cereblon-binding compound. As used herein, "transmembrane domain" includes pass-through transmembrane domains in which the protein comprising the transmembrane domain comprises both intracellular and extracellular domains, and membrane-anchoring domains in which the protein comprising the transmembrane domain comprises an intracellular domain but not an extracellular domain.

In a specific embodiment, provided herein is a CAR comprising (a) a first polypeptide comprising an antigen-binding domain, a transmembrane domain, and cereblon or a functional portion thereof, wherein said cereblon (or functional portion thereof) is capable of binding to a cereblon-binding compound; and (b) a second polypeptide comprising a transmembrane domain, a cereblon-associated protein or a functional portion thereof, wherein said cereblon-associated protein (or functional portion thereof) is capable of binding a cereblon-binding compound, and a primary cell signaling domain; wherein in the presence of said cereblon-binding compound, said first polypeptide and said second polypeptide form a heterodimer. In a specific embodiment, the cereblon-associated protein is Aiolos or Ikaros.

In another specific embodiment, provided herein is a CAR comprising (a) a first polypeptide comprising, in order from N-terminus to C-terminus, an antigen-binding domain, a transmembrane domain, and cereblon or a functional portion thereof, and (b) a second polypeptide comprising, in order from N-terminus to C-terminus, a transmembrane domain, a cereblon-associated protein or a functional portion thereof, and a primary T cell signaling domain. In a specific embodiment, the cereblon-associated protein is Aiolos or Ikaros. In another specific embodiment, the first polypeptide comprises a costimulatory domain. In another specific embodiment, the second polypeptide comprises a costimulatory domain. In another specific embodiment, the first polypeptide and the second polypeptide comprise a costimulatory domain. In another specific embodiment, the first polypeptide comprises a costimulatory domain and the second polypeptide does not comprise a costimulatory domain. In another specific embodiment, the second polypeptide comprises a costimulatory domain and the first polypeptide does not comprise a costimulatory domain. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, cereblon or a functional portion thereof, and a transmembrane domain, and (b) a second polypeptide comprising, in order from N-terminus to C-terminus, a cereblon-associated protein or a functional portion thereof, a transmembrane domain, and a primary T cell signaling domain. In a specific embodiment, the cereblon-associated protein is Aiolos or Ikaros. In another specific embodiment, the first polypeptide comprises a costimulatory domain. In another specific embodiment, the second polypeptide comprises a costimulatory domain. In another specific embodiment, the first polypeptide and the second polypeptide comprise a costimulatory domain. In another specific embodiment, the first polypeptide comprises a costimulatory domain and the second polypeptide does not comprise a costimulatory domain. In another specific embodiment, the second polypeptide comprises a costimulatory domain and the first polypeptide does not comprise a costimulatory domain. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising an antigen-binding domain, a transmembrane domain, and a cereblon-associated protein or a functional portion thereof, wherein said cereblon-associated protein (or functional portion thereof) is capable of binding to a cereblon-binding compound; and (b) a second polypeptide comprising a transmembrane domain, cereblon or a functional portion thereof, wherein said cereblon (or functional portion thereof) is capable of binding a cereblon-binding compound, and a primary cell signaling domain; wherein in the presence of said cereblon-binding compound, said first polypeptide and said second polypeptide form a heterodimer. In a specific embodiment, the cereblon-associated protein is Aiolos or Ikaros. In a specific embodiment, said cereblon-binding compound is pomalidomide (4-amino-2-[(3RS)-(2,6-dioxopiperidin-3-yl)-1H-isoindole-1,3 (2H)-dione). In another specific embodiment, said cereblon-binding compound is thalidomide ((RS)-2-(2,6-dioxopiperidin-3-yl)-1H-isoindole-1,3(2H)-dione). In another specific embodiment, said cereblon-binding compound is lenalidomide (3-(4-amino-1-oxo-1,3-dihydro-2H-isoindol-2-yl)piperidine-2,6-dione). In another specific embodiment, said cereblon-binding compound is 3-[4-(4-morpholin-4-ylmethyl-benzyloxy)-1-oxo-1,3-dihydro-Isoindol-2-yl]-piperidine-2,6-dione. In another specific embodiment, said cereblon-binding compound is 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, a transmembrane domain, and cereblon-associated protein or a functional portion thereof, and (b) a second polypeptide comprising, in order from N-terminus to C-terminus, a transmembrane domain, cereblon or a functional portion thereof, and a primary T cell signaling domain. In a specific embodiment, the cereblon-associated protein is Aiolos or Ikaros. In a specific embodiment, the first polypeptide comprises a costimulatory domain. In another specific embodiment, the second polypeptide comprises a costimulatory domain. In another specific embodiment, the first polypeptide and the second polypeptide comprise a costimulatory domain. In another specific embodiment, the first polypeptide comprises a costimulatory domain and the second polypeptide does not comprise a costimulatory domain. In another specific embodiment, the second polypeptide comprises a costimulatory domain and the first polypeptide does not comprise a costimulatory domain. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, a cereblon-associated protein or a functional portion thereof, and a transmembrane domain, and (b) a second polypeptide comprising, in order from N-terminus to C-terminus, cereblon or a functional portion thereof, a transmembrane domain, and a primary T cell signaling domain. In a specific embodiment, the cereblon-associated protein is Aiolos or Ikaros. In another specific embodiment, the first polypeptide comprises a costimulatory domain. In another specific embodiment, the second polypeptide comprises a costimulatory domain. In another specific embodiment, the first polypeptide and the second polypeptide comprise a costimulatory domain. In another specific embodiment, the first polypeptide comprises a costimulatory domain and the second polypeptide does not comprise a costimulatory domain. In another specific embodiment, the second polypeptide comprises a costimulatory domain and the first polypeptide does not comprise a costimulatory domain. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, a transmembrane domain, cereblon or a functional portion thereof, and a primary cell signaling domain, and (b) a second polypeptide comprising, in order from N-terminus to C-terminus, a transmembrane domain, a cereblon-associated protein or a functional portion thereof, and a costimulatory domain. In a specific embodiment, the cereblon-associated protein is Aiolos or Ikaros. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, cereblon or a functional portion thereof, a transmembrane domain, and a polypeptide comprising a primary cell signaling domain, and (b) a second polypeptide comprising, in order from N-terminus to C-terminus, a cereblon-associated protein or a functional portion thereof, a transmembrane domain, and a costimulatory domain. In a specific embodiment, the cereblon-associated protein is Aiolos or Ikaros. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, a transmembrane domain, a cereblon-associated protein or a functional portion thereof, and a primary cell signaling domain, and (b) a second polypeptide comprising, in order from N-terminus to C-terminus, a transmembrane domain, cereblon or a functional portion thereof, and a costimulatory domain. In a specific embodiment, the cereblon-associated protein is Aiolos or Ikaros. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

In another specific embodiment, provided herein is a CAR comprising (a) a first polypeptide comprising, in order from N-terminus to C-terminus, an antigen-binding domain, a cereblon-associated protein or a functional portion thereof, a transmembrane domain, and a polypeptide comprising a primary cell signaling domain, and (b) a second polypeptide comprising, in order from N-terminus to C-terminus, cereblon or a functional portion thereof, a transmembrane domain, and a costimulatory domain. In a specific embodiment, the cereblon-associated protein is Aiolos or Ikaros. In another embodiment, said cereblon (or functional portion thereof) and said cereblon-associated protein (or functional portion thereof) are both capable of binding a cereblon-binding compound, wherein said cereblon-binding compound is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

Cereblon and Cereblon-Associated Proteins

The CARs provided herein comprise polypeptides comprising cereblon or a functional portion thereof or a cereblon-associated protein (e.g., Aiolos or Ikaros), or a functional portion of either thereof. As used herein, the term "functional portion" of cereblon or a cereblon-associated protein is defined as a portion of cereblon or a cereblon-associated protein that is capable of binding a cereblon-binding compound. In some embodiments, a functional portion of cereblon or a cereblon-associated protein comprises the full polypeptide coding sequence of said cereblon or said cereblon-associated protein. In other embodiments, a functional portion of cereblon or a cereblon-associated protein comprises a truncation of said cereblon or said cereblon-associated protein, respectively. One of skill in the art will recognize the components of each protein required to maintain function and/or to ensure binding of each protein to a cereblon-binding compound. In other embodiments, a functional portion of cereblon or a cereblon-associated protein comprises a peptide sequence derived from said cereblon or said cereblon-associated protein, respectively. One of skill in the art will recognize the components of each protein required to maintain function and/or to ensure binding of each protein to a cereblon-binding compound.

In some embodiments, a CAR provided herein comprises a polypeptide comprising cereblon or a functional portion thereof, which is capable of binding a cereblon-binding compound. In some embodiments, a CAR provided herein comprises a polypeptide comprising a cereblon-associated protein (e.g., Aiolos or Ikaros) or a functional portion thereof, which is capable of binding a cereblon-binding compound. In some embodiments, a CAR provided herein comprises a polypeptide comprising Aiolos or a functional portion thereof, which is capable of binding a cereblon-binding compound. In specific embodiments, a CAR provided herein comprises: (i) a first polypeptide comprising cereblon or a functional portion thereof, which is capable of binding a cereblon-binding compound, and (ii) a second polypeptide comprising cereblon-associated protein (e.g., Aiolos or Ikaros) or a functional portion thereof, which is capable of binding a cereblon-binding compound.

Cereblon is also known as the protein "mental retardation, non-syndromic, autosomal recessive, 2A," CRBN, MRT2, MRT2A, and AD-006. An exemplary nucleic acid encoding cereblon is provided, e.g., under Genbank Gene ID: 51185. An exemplary cereblon amino acid sequence is provided, e.g., under Uniprot ID: Q96SW2-1. One of skill in the art will readily appreciate how to make and use cereblon-containing polypeptides using recombinant engineering. As used herein, the term "cereblon" refers to a naturally occurring cereblon protein or portions thereof, as well as polypeptides comprising at least 80%, 85%, 90%, 95%, 96%, 97%, 98%, or 99% homology or sequence identity to a naturally occurring cereblon protein or a portion thereof, wherein the sequence can bind a cereblon-associated protein, e.g., in the presence of a cereblon binding compound described herein.

As used herein "cereblon-associated proteins" refer to proteins (or portions thereof) that serve as substrates of cereblon, e.g., can bind to and/or associate with cereblon, e.g., in the presence of a cereblon binding compound. See, e.g., Gandhi et al., 2014, Br. J. Haematol. 164(6):811-821.

In a specific embodiment, the cereblon-associated protein used in the CARs described herein is Aiolos. Aiolos is also known as "IKAROS family zinc finger 3," "zinc finger protein, subfamily 1A, 3," and ZNFN1A3. An exemplary nucleic acid encoding Aiolos is provided under Genbank Gene ID: 22806. An exemplary Aiolos amino acid sequence is provided, e.g., under Uniprot ID: Q9UKT9-1. One of skill in the art will readily appreciate how to make and use Aiolos-containing polypeptides using recombinant engineering. As used herein, the term "Aiolos" refers to a naturally occurring Aiolos protein or portions thereof, as well as polypeptides comprising at least 80%, 85%, 90%, 95%, 96%, 97%, 98%, or 99% homology or sequence identity to a naturally occurring Aiolos protein or a portion thereof.

In another specific embodiment, the cereblon-associated protein used in the CARs described herein is Ikaros. Ikaros is also known as "IKAROS family zinc finger 1," IKZF1, IK1, LYF1, LyF-1, CVID13, PPP1R92, PRO0758, ZNFN1A1 and Hs.54452. An exemplary nucleic acid encoding Ikaros is provided, e.g., under Genbank Gene ID: 10320. An exemplary Ikaros amino acid sequence is provided, e.g., under Uniprot ID: Q03267-1. One of skill in the art will readily appreciate how to make and use Ikaros-containing polypeptides using recombinant engineering. As used herein, the term "Ikaros" refers to a naturally occurring Ikaros protein or portions thereof, as well as polypeptides comprising at least 80%, 85%, 90%, 95%, 96%, 97%, 98%, or 99% homology or sequence identity to a naturally occurring Ikaros protein or a portion thereof.

Antigen-Binding Domain

The antigen binding domains of the CARs provided herein can be any polypeptide domain, motif or sequence that binds to an antigen.

In certain embodiments, the antigen binding domain of the CARs described herein is an antigen binding portion of a receptor. In a specific embodiment, the antigen binding domain of the CARs described herein is a receptor for a ligand produced by a tumor cell.

In certain embodiments, the antigen binding domain of the CARs described herein is an antigen-binding portion of an antibody. In a specific embodiment, the antigen binding domain of the CARs described herein is an antibody, an antibody chain, a single chain antibody, or an antigen binding portion thereof, an Fc domain, a glycophosphatidylinositol anchor domain, or scFv antibody fragment.

In certain embodiments, the antigen binding domain of the CARs described herein is a peptide-based macromolecular antigen binding agent, e.g., a phage display protein.

In certain embodiments, antigen binding by an antigen binding domain of a CAR described herein is restricted to antigen presentation in association with major histocompatibility complexes (MHC). In certain embodiments, antigen binding by an antigen binding domain of a CAR described herein is MHC-unrestricted.

The antigen bound/recognized by the antigen binding domain of the CARs described herein can be any antigen of interest. In a specific embodiment, the antigen is an antigen that is expressed on the surface of a cell (e.g., a tumor cell, such as a solid tumor cell or a blood cancer tumor cell).

In a specific embodiment, the antigen bound/recognized by the antigen binding domain of the CARs described herein is an antigen on a tumor cell, for example, the antigen is a TSA or a TAA. Exemplary tumor cell antigens that can be recognized by the CARs described herein (i.e., bound by the antigen-binding domain of the CARs) include, without limitation, 4-1BB, 5T4, 8H9, B7-H6, adenocarcinoma antigen, α-fetoprotein, B Cell Maturation Antigen (BCMA), BAFF, B-lymphoma cell, C242 antigen, CA9, carcinoembryonic antigen, CA-125, carbonic anhydrase 9 (CA-IX), CCR4, CD3, CD4, CD19, CD20, CD22, CD23 (IgE receptor), CD28, CD30 (TNFRSF8), CD33, CD38, CD40, CD44v6, CD44v7/8, CD51, CD52, CD56, CD74, CD80, CD123, CD152, CD171, CD200, CD221, CE7, CEA, C-MET, CNT0888, CTLA-4, DR5, EpCAM, ErbB2, ErbB3/4, EGFR, EGFRvIII, EphA2, EGP2, EGP40, FAP, Fetal AchR, fibronectin extra domain-B, folate receptor-a, folate receptor 1, G250/CAIX, GD2, GD3, glycoprotein 75, GPNMB, HER2/neu, HGF, HLA-AI MAGE A1, HLA-A2 NY-ESO-1, HMW-MAA, human scatter factor receptor kinase, IGF-1 receptor, IGF-I, IgGl, IL-6, IL-13, IL-13 receptor a2, IL-11 receptor a, insulin-like growth factor I receptor, integrin a5I31, integrin avI33, Kappa light chain, L1-CAM, Lambda light chain, Lewis Y, mesothelin, MORAb-009, MS4A1, MUC1, MUC16, mucin CanAg, NCAM, N-glycolylneuraminic acid, NKG2D ligands, NPC-1C, PDGF-R a, PDL192, phosphatidylserine, prostate-specific cancer antigen (PSCA), prostatic carcinoma cells, PSMA, PSC1, RANKL, RON, ROR1, SCH 900105, SDC1, SLAMF7, sp17, TAG72, tenascin C, TGF β2, TGF-I3, TL1A, TRAIL-R1, TRAIL-R2, tumor antigen CTAA16.88, VEGF-A, VEGF receptors, VEGFR-1, VEGFR2, TEM1, TEM8, and vimentin.

In another specific embodiment, the antigen bound/recognized by the antigen binding domain of the CARs described herein is an antigen expressed on or associated with a tumor cell of a lymphoma/leukemia, a lung cancer, a breast cancer, a prostate cancer, an adrenocortical carcinoma, a thyroid carcinoma, a nasopharyngeal carcinoma, a melanoma, e.g., a malignant melanoma, a skin carcinoma, a colorectal carcinoma, a desmoid tumor, a desmoplastic small round cell tumor, an endocrine tumor, an Ewing sarcoma, a peripheral primitive neuroectodermal tumor, a solid germ cell tumor, a hepatoblastoma, a neuroblastoma, a non-rhabdomyosarcoma soft tissue sarcoma, an osteosarcoma, a retinoblastoma, a rhabdomyosarcoma, a Wilms tumor, a glioblastoma, a myxoma, a fibroma, a lipoma, or the like.

In another specific embodiment, the antigen bound/recognized by the antigen binding domain of the CARs described herein is an antigen expressed on or associated with a tumor cell of chronic lymphocytic leukemia (small lymphocytic lymphoma), B-cell prolymphocytic leukemia, lymphoplasmacytic lymphoma, Waldenstrom macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma.

In another specific embodiment, the antigen bound/recognized by the antigen binding domain of the CARs described herein is a non-tumor-associated antigen or a non-tumor-specific antigen. In certain embodiments, the antigen is related to an aspect of a tumor, e.g., the tumor environment. For example, a tumor can induce an inflammatory state in tissue surrounding the tumor, and can release angiogenic growth factors, interleukins, and/or cytokines that promote angiogenesis into and at the periphery of the tumor. Thus, in certain embodiments, the antigen is a growth factor, a cytokine, or an interleukin (e.g., a growth factor, cytokine, or interleukin associated with angiogenesis or vasculogenesis). Such growth factors, cytokines, and interleukins can include, without limitation, vascular endothelial growth factor (VEGF), basic fibroblast growth factor (bFGF), platelet-derived growth factor (PDGF), hepatocyte growth factor (HGF), insulin-like growth factor (IGF), and interleukin-8 (IL-8).

In another specific embodiment, the antigen bound/recognized by the antigen binding domain of the CARs described herein is a damage associated molecular pattern molecule (DAMP; also known as an alarmin) released by normal tissue in response to localize damage caused by a tumor. Exemplary DAMPs to which the antigen-binding domain of the CARs described herein can bind include, without limitation, heat shock protein, chromatin-associated protein high mobility group box 1 (HMGB1), S100A8 (MRP8, calgranulin A), S100A9 (MRP14, calgranulin B), serum amyloid A (SAA), deoxyribonucleic acid, adenosine triphosphate, uric acid, and heparin sulfate.

Transmembrane Domain

The transmembrane domains of the CARs described herein can comprise any molecule known in the art to function as a transmembrane domain, e.g., known by one of skill in the art to function in the CAR context. The transmembrane domains of the CARs described herein can be obtained or derived from the transmembrane domain of any transmembrane protein, and can include all or a portion of such transmembrane domain.

In a specific embodiment, the transmembrane domain of the first and/or second polypeptide of the CARs described herein is obtained or derived from a T-cell receptor, e.g., the transmembrane domain of the first and/or second polypeptide of the CARs described herein is obtained or derived from the alpha chain of a T-cell receptor, the beta chain of a T-cell receptor, the zeta chain of a T-cell receptor.

In specific embodiments, the transmembrane domain of the first and/or second polypeptide of the CARs described herein is obtained or derived from CD28, CD3ε, CD45, CD4, CD5, CD8, CD9, CD16, CD22, CD33, CD37, CD64, CD80, CD86, CD134, CD137 or CD154, a cytokine receptor, an interleukin receptor, or a growth factor receptor.

Signaling Domain

The primary cell signaling domain of the CARs described herein can comprise any molecule known in the art to function as a cell signaling domain, e.g., known by one of skill in the art to function in the CAR context. In a specific embodiment, the cell signaling domain of the CARs described herein comprises a primary T cell signaling domain.

In a specific embodiment, the primary cell signaling domain of the CARs described herein is or comprises ZAP-70, or a signal-transducing variant thereof.

In another specific embodiment, the primary cell signaling domain of the CARs described herein is or comprises an ITAM. In a specific embodiment, said ITAM is the ITAM of FcRγ, FcRβ, CD3ζ, CD3γ, CD3δ, CD3ε, CD5, CD22, CD79a, CD79b, CD278 (ICOS), FcERI, CD66d, DAP10, or DAP12.

Costimulatory Domain

In certain embodiments, the first and/or second polypeptides of the CARs described herein comprise a costimulatory domain. The costimulatory domain(s) of the CARs described herein can comprise any molecule known in the art to function as a costimulatory domain, e.g. known by one of skill in the art to function in the CAR context.

In a specific embodiment, the costimulatory domain of the first and/or second polypeptide of the CARs described herein is obtained or derived from a costimulatory CD27 polypeptide sequence, a costimulatory CD28 polypeptide sequence, a costimulatory OX40 (CD134) polypeptide sequence, a costimulatory 4-1BB (CD137) polypeptide sequence, or a costimulatory inducible T-cell costimulatory (ICOS) polypeptide sequence.

In another specific embodiment, the costimulatory domain of the first and/or second polypeptide of the CARs described herein is or comprises CD28, 4-1BB (CD137), OX40, an activating NK cell receptor, BTLA, a Toll ligand receptor, CD2, CD7, CD27, CD30, CD40, CDS, ICAM-L LFA-1 (CD11a/CD18), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8α, CD8β, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD1c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, DAP10, DAP12, a ligand of CD83, an MHC class I molecule, a TNF receptor protein, an immunoglobulin-like protein, a cytokine receptor, an integrin, or a signaling lymphocytic activation molecule.

Other Modifications

In certain embodiments, the first and/or second polypeptide of the CARs described herein further comprise a dimerization domain that is responsive to a modulating agent (i.e., an agent other than a cereblon-binding compound).

In certain embodiments, the first and/or second polypeptide of the CARs described herein further comprise a T cell survival motif. The T cell survival motif can be any polypeptide sequence or motif that facilitates the survival of a T lymphocyte after stimulation by an antigen. In certain embodiments, the T cell survival motif is, or is derived from, CD3ζ, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor 1 (TGFβ) receptor.

4.1.2. CAR Polypeptide Modifications

In certain embodiments, the first and/or second polypeptides of the CARs provided herein are modified by, e.g., acylation, amidation, glycosylation, methylation, phosphorylation, sulfation, sumoylation, and/or ubiquitylation (or other protein modifications).

In certain embodiments, the first and/or second polypeptides of the CARs provided herein are labeled with a label capable of providing a detectable signal, e.g., a radioisotope or fluorescent compound.

In certain embodiments, one or more side chains of the first and/or second polypeptides of the CARs provided herein are derivatized, e.g., derivatization of lysinyl and amino terminal residues with succinic or other carboxylic acid anhydrides, or derivatization with, e.g., imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. In certain embodiments, carboxyl side groups, aspartyl or glutamyl, may be selectively modified by reaction with carbodiimides (R—N=C=N—R') such as 1-cyclohexyl-3-(2-morpholinyl-(4-ethyl)carbodiimide or 1-ethyl-3-(4-azonia-4,4-dimethylpentyl)carbodiimide.

4.1.3. Nucleic Acids

Provided herein are nucleic acids encoding the CARs described herein, i.e., nucleic acids encoding the first polypeptide and nucleic acids encoding the second polypeptide of the CARs described herein. In certain embodiments, a first polypeptide of a CAR described herein is encoded by a first nucleic acid (polynucleotide) and the second polypeptide of a CAR described herein is encoded by a second nucleic acid (polynucleotide). In a specific embodiment, provided herein is a nucleic acid (polynucleotide) that encodes both the first polypeptide and second polypeptide of a CAR described herein.

Nucleic acids useful in the production of the CARs described herein include DNA, RNA, and nucleic acid analogs. Nucleic acid analogs can be modified at the base moiety, sugar moiety, or phosphate backbone, and can include deoxyuridine substitution for deoxythymidine, 5-methyl-2'-deoxycytidine or 5-bromo-2'-deoxycytidine substitution for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) Antisense Nucleic Acid Drug Dev. 7:187-195; and Hyrup et al. (1996) Bioorgan. Med. Chain. 4:5-23. In addition, the deoxyphosphate backbone can be replaced with, for example, a phosphorothioate or phosphorodithioate backbone, a phosphoroamidite, or an alkyl phosphotriester backbone.

In certain embodiments, the CAR polypeptide-encoding nucleic acids described herein are comprised within a nucleic acid vector. For example, cells of interest, e.g., T lymphocytes, can be transformed using synthetic vectors, lentiviral or retroviral vectors, autonomously replicating plasmids, a virus (e.g., a retrovirus, lentivirus, adenovirus, or herpes virus), or the like, containing nucleic acid (polynucleotides) encoding the first and/or second polypeptides of the CARs described herein. In a specific embodiment, the vector comprising the first and/or second polypeptides of the CARs described herein is a retroviral vector. In another specific embodiment, the vector comprising the first and/or second polypeptides of the CARs described herein is a lentiviral vector. Lentiviral vectors suitable for transformation of cells, e.g., T lymphocytes, include, but are not limited to the lentiviral vectors described in U.S. Pat. Nos. 5,994,136; 6,165,782; 6,428,953; 7,083,981; and 7,250,299. HIV vectors suitable for transformation of cells, e.g., T lymphocytes, include, but are not limited to the vectors described in U.S. Pat. No. 5,665,577.

In certain embodiments, the CAR polypeptide-encoding nucleic acids described herein are operably linked to a promoter. In a specific embodiment, said promoter is a T cell-specific promoter, a natural killer (NK) cell-specific promoter, an inducible promoter that functions within T cells or NK cells, or a constitutive promoter.

4.1.4. Cells

The CARs provided herein can be expressed in cells for which CAR expression is useful, i.e., cells are engineered to comprise a CAR-encoding nucleic acid provided herein, such that, upon expression of the nucleic acid in the cell, the cell expresses a CAR described herein. For example, the CARs described herein can be expressed in T lymphocytes or natural killer cells. Cells provided herein that express the CARs described herein are referred to as "CAR cells."

In certain embodiments, provided herein is a cell (e.g., a T lymphocyte or a natural killer cell) that has been modified to express a CAR that comprises: (i) a first polypeptide comprising cereblon or a functional portion thereof, which is capable of binding a cereblon-binding compound, and (ii) a second polypeptide comprising a cereblon-associated protein (e.g., Aiolos or Ikaros) or a functional portion thereof, which is capable of binding a cereblon-binding compound. In a specific embodiment, the first polypeptide further comprises an antigen-binding domain and a transmembrane domain (and, optionally, a costimulatory domain). In a specific embodiment, the second polypeptide further comprises a transmembrane domain and a primary cell signaling domain (and, optionally, a costimulatory domain).

In a specific embodiment, the CARs provided herein are expressed in T lymphocytes. The T lymphocytes can be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T lymphocytes have been isolated from, or are expanded from T lymphocytes expanded from, peripheral blood, cord blood, or lymph.

In a specific embodiment, the cells (e.g., T lymphocytes) engineered to comprise/express a CAR described herein are autologous to an individual to whom the cells (e.g., T lymphocytes) are to be administered as part of a method of treatment described herein. In other embodiments, the cells (e.g., T lymphocytes) engineered to comprise/express a CAR described herein are allogeneic to an individual to whom the cells (e.g., T lymphocytes) are to be administered. Where allogeneic cells (e.g., T lymphocytes) are used to prepare CAR cells, it is preferable to select cells (e.g., T lymphocytes) that will reduce the possibility of graft-versus-host disease (GVHD) in the individual. For example, in certain embodiments, virus-specific T lymphocytes are selected for preparation of CAR T lymphocytes; such lymphocytes will be expected to have a greatly reduced native capacity to bind to, and thus become activated by, any recipient antigens. In certain embodiments, recipient-mediated rejection of allogeneic cells (e.g., T lymphocytes) can be reduced by co-administration to the host of one or more immunosuppressive agents, e.g., cyclosporine, tacrolimus, sirolimus, cyclophosphamide, or the like.

In one embodiment, T lymphocytes are obtained from an individual, optionally then expanded, and then transformed with a first vector encoding the first polypeptide of a CAR described herein and a second vector encoding the second polypeptide of a CAR described herein, and optionally then expanded. Double transformants may be selected using, e.g., a selectable marker unique to each of the vectors.

In another embodiment, T lymphocytes are obtained from an individual, optionally then expanded, and then transformed with a vector encoding the first polypeptide and the second polypeptide of a CAR described herein, and optionally then expanding. Cells containing the vector can be obtained using a selectable marker.

In certain embodiments, the T lymphocytes used to generate CAR cells provided herein comprise native TCR proteins, e.g., TCR-α and TCR-β that are capable of forming native TCR complexes, in addition to an artificial costimulatory polypeptide (in embodiments in which a costimulatory polypeptide is used), or in addition to the first polypeptide and second polypeptide (in embodiments in which the CAR cells comprise polypeptides separating the antigen binding signaling and costimulatory signaling). In certain other embodiments, either or both of the native genes encoding TCR-α and TCR-β in the T lymphocytes are modified to be non-functional, e.g., a portion or all are deleted or a mutation is inserted.

In certain embodiments, the signaling domain(s) of a CAR described herein can be used to promote proliferation and expansion of cells (e.g., T lymphocytes) comprising/expressing the CAR. For example, unmodified T lymphocytes, and T lymphocytes comprising a polypeptide comprising a CD3ζ signaling domain and a CD28 costimulatory domain can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681. Similarly, antibodies to a signaling motif can be used to stimulate proliferation of cell (e.g., T lymphocytes) comprising a CAR described herein.

In certain embodiments, the CAR cells described herein comprise a "suicide gene" or "safety switch" that enables killing of substantially all of the CAR cells when desired. For example, CAR cells described herein, in certain embodiments, comprise an HSV thymidine kinase gene (HSV-TK), which causes cell death upon contact with gancyclovir. In another embodiment, the CAR cells comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., Blood 105 (11):4247-4254 (2005).

In certain embodiments, the CAR cells provided herein further comprise an artificial cell death polypeptide comprising an apoptosis-inducing domain and a dimerization domain, wherein the artificial cell death polypeptide is dimerizable using a dimerizing agent, and wherein when the artificial cell death polypeptide is dimerized, the polypeptide generates an apoptosis-inducing signal in said cell. In a specific embodiment, said dimerizing agent is rapamycin or an analog of rapamycin (rapalog). In another specific embodiment, said dimerizing agent is AP1903 (rimiducid). In another specific embodiment, said dimerizing agent is not a cereblon-binding compound. In a specific embodiment, said dimerization domain is FK binding domain or an analog thereof. In another specific embodiment, said dimerizing agent is an antibody that binds to said FK binding domain.

4.1.5. Methods of Use

The CAR cells provided herein, e.g., T lymphocytes modified to comprise/express a CAR described herein, can be used to treat an individual having one or more types of cells desired to be targeted by the cells, e.g., to be killed.

In a specific embodiment, provided herein are methods for killing target cells that express an antigen bound by the antigen-binding domain of a CAR described herein, wherein said methods comprise (i) contacting said target cells with a cell (e.g., a T cell or NK cell) comprising/expressing a CAR described herein and (ii) contacting said CAR-expressing cell with a cereblon-binding compound, wherein in the presence of said antigen and said cereblon-binding compound the CAR-expressing cell becomes activated. In a specific embodiment, said target cell is a cancer cell, e.g., a blood cancer cell or a solid tumor cell. In another specific embodiment, said target cell expresses one or more the following antigens, or a fragment thereof: 4-1BB, 5T4, 8H9, B7-H6, adenocarcinoma antigen, α-fetoprotein, B Cell Maturation Antigen (BCMA), BAFF, B-lymphoma cell, C242 antigen, CA9, carcinoembryonic antigen, CA-125, carbonic anhydrase 9 (CA-IX), CCR4, CD3, CD4, CD19, CD20, CD22, CD23 (IgE receptor), CD28, CD30 (TNFRSF8), CD33, CD38, CD40, CD44v6, CD44v7/8, CD51, CD52, CD56, CD74, CD80, CD123, CD152, CD171, CD200, CD221, CE7, CEA, C-MET, CNT0888, CTLA-4, DRS, EpCAM, ErbB2, ErbB3/4, EGFR, EGFRvIII, EphA2, EGP2, EGP40, FAP, Fetal AchR, fibronectin extra domain-B, folate receptor-a, folate receptor 1, G250/CAIX, GD2, GD3, glycoprotein 75, GPNMB, HER2/neu, HGF, HLA-AI MAGE A1, HLA-A2 NY-ESO-1, HMW-MAA, human scatter factor receptor kinase, IGF-1 receptor, IGF-I, IgGl, IL-6, IL-13, IL-13 receptor a2, IL-11 receptor a, insulin-like growth factor I receptor, integrin a5I31, integrin avI33, Kappa light chain, L1-CAM, Lambda light chain, Lewis Y, mesothelin, MORAb-009, MS4A1, MUC1, MUC16, mucin CanAg, NCAM, N-glycolylneuraminic acid, NKG2D ligands, NPC-1C, PDGF-R a, PDL192, phosphatidylserine, prostate-specific cancer antigen (PSCA), prostatic carcinoma cells, PSMA, PSC1, RANKL, RON, ROR1, SCH 900105, SDC1, SLAMF7, sp17, TAG72, tenascin C, TGF β2, TGF-I3, TL1A, TRAIL-R1, TRAIL-R2, tumor antigen CTAA16.88, VEGF-A, VEGF receptors, VEGFR-1, VEGFR2, TEM1, TEM8, and/or vimentin.

In another specific embodiment, provided herein are methods of treating cancer, said methods comprising (i) administration of a population of CAR cells described herein, e.g., a T cells or NK cells, that comprise/express a CAR described herein (e.g., comprise a CAR-encoding nucleic acid(s) described herein or express a CAR described herein), wherein said CAR comprises an antigen-binding domain specific for a cancer antigen (e.g., TSA or TAA) to a subject (for example, a human subject) and (ii) administering to the subject a composition comprising cereblon-binding compound. In a specific embodiment, said population of cells is administered first to the subject, followed by administration of the composition comprising a cereblon-binding compound at a specified period of time after administration of the cell population, e.g., 30 minutes, 1 hour, 6 hours, 12 hours, 1 day, 2 days, 3 days, 4 days, 5 days, 6 days, or 1 week after administration of the cell population. In a specific embodiment, said antigen bound by said CAR is 4-1BB, 5T4, 8H9, B7-H6, adenocarcinoma antigen, α-fetoprotein, B Cell Maturation Antigen (BCMA), BAFF, B-lymphoma cell, C242 antigen, CA9, carcinoembryonic antigen, CA-125, carbonic anhydrase 9 (CA-IX), CCR4, CD3ζ, CD4, CD19, CD20, CD22, CD23 (IgE receptor), CD28, CD30 (TNFRSF8), CD33, CD38, CD40, CD44v6, CD44v7/8, CD51, CD52, CD56, CD74, CD80, CD123, CD152, CD171, CD200, CD221, CE7, CEA, C-MET, CNT0888, CTLA-4, DRS, EpCAM, ErbB2, ErbB3/4, EGFR, EGFRvIII, EphA2, EGP2, EGP40, FAP, Fetal AchR, fibronectin extra domain-B, folate receptor-a, folate receptor 1, G250/CAIX, GD2, GD3, glycoprotein 75, GPNMB, HER2/neu, HGF, HLA-AI MAGE A1, HLA-A2 NY-ESO-1, HMW-MAA, human scatter factor receptor kinase, IGF-1 receptor, IGF-I, IgGl, IL-6, IL-13, IL-13 receptor a2, IL-11 receptor a, insulin-like growth factor I receptor, integrin a5I31, integrin avI33, Kappa light chain, L1-CAM, Lambda light chain, Lewis Y, mesothelin, MORAb-009, MS4A1, MUC1, MUC16, mucin CanAg, NCAM, N-glycolylneuraminic acid, NKG2D ligands, NPC-1C, PDGF-R a, PDL192, phosphatidylserine, prostate-specific cancer antigen (PSCA), prostatic carcinoma cells, PSMA, PSC1, RANKL, RON, ROR1, SCH 900105, SDC1, SLAMF7, sp17, TAG72, tenascin C, TGF β2, TGF-I3, TL1A, TRAIL-R1, TRAIL-R2, tumor antigen CTAA16.88, VEGF-A, VEGF receptors, VEGFR-1, VEGFR2, TEM1, TEM8, and/or vimentin.

In a specific embodiment, the cereblon-binding compound administered to a subject in accordance with the methods of treating cancer described herein is pomalidomide, thalidomide, lenalidomide, 3-[4-(4-morpholin-4-ylm-ethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

A non-limiting list of cancers that can be treated in accordance with the methods of treatment described herein includes lymphoma, leukemia, lung cancer, breast cancer, prostate cancer, adrenocortical carcinoma, thyroid carcinoma, nasopharyngeal carcinoma, melanoma, skin carcinoma, colorectal carcinoma, desmoid tumor, aesmoplastic small round cell tumor, endocrine tumor, Ewing sarcoma, peripheral primitive neuroectodermal tumor, solid germ cell tumor, hepatoblastoma, neuroblastoma, non-rhabdomyosarcoma soft tissue sarcoma, osteosarcoma, retinoblastoma, rhabdomyosarcoma, Wilms tumor, glioma, glioblastoma, myxoma, fibroma, and lipoma. Exemplary lymphomas and leukemias include, without limitation, chronic lymphocytic leukemia (small lymphocytic lymphoma), B-cell prolymphocytic leukemia, lymphoplasmacytic lymphoma, Waldenstrom macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma.

Efficacy of the CAR cells described herein in treatment of a disease or disorder, e.g., in treatment of an individual having cancer, can be assessed by one or more criteria specific to the particular disease or disorder, known to those of ordinary skill in the art, to be indicative of progress of the disease or disorder. Generally, administration of CAR cells (e.g., CAR T lymphocytes) to an individual having a disease/disorder (e.g., cancer) is effective when one or more of said criteria detectably, e.g., significantly, moves from a disease state value or range to, or towards, a normal value or range.

The CAR cells described herein can be formulated in any pharmaceutically-acceptable solution, preferably a solution suitable for the delivery of living cells, e.g., saline solution (such as Ringer's solution), gelatins, carbohydrates (e.g., lactose, amylose, starch, or the like), fatty acid esters, hydroxymethylcellulose, polyvinyl pyrolidine, etc. Such preparations are preferably sterilized prior to addition of the CAR cells, and may be mixed with auxiliary agents such as lubricants, preservatives, stabilizers, emulsifiers, salts for influencing osmotic pressure, buffers, and coloring. Pharmaceutical carriers suitable for use in formulating the CAR cells described herein are known in the art and are described, for example, in WO 96/05309.

In certain embodiments, the CAR cells (e.g., CAR T lymphocytes) described herein are formulated into individual doses, wherein said individual doses comprise at least, at most, or about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$ $1\times10^{10}$, $5\times10^{10}$, or $1\times10^{11}$ CAR cells.

In certain embodiments, the CAR cells (e.g., CAR T lymphocytes) described herein are formulated for intravenous, intraarterial, parenteral, intramuscular, subcutaneous, intrathecal, or intraocular administration, or administration within a particular organ or tissue.

Cereblon-Binding Compounds

As used herein, the term "cereblon-binding compound" refers to a molecule (e.g., a small molecule or protein/polypeptide (e.g., an antibody)) capable of binding cereblon (or functional portion thereof) and capable of binding a cereblon-associated protein (or functional portion thereof), e.g., Aiolos, (or functional portion thereof) or Ikaros (or functional portion thereof). In a specific embodiment, a cereblon-binding compound is capable of binding both cereblon (or functional portion thereof) and Aiolos (or functional portion thereof), resulting in an association between cereblon (or functional portion thereof) and Aiolos (or functional portion thereof), e.g., the formation of a heterodimer. In another specific embodiment, a cereblon-binding compound is capable of binding both cereblon (or functional portion thereof) and Ikaros (or functional portion thereof), resulting in an association between cereblon (or functional portion thereof) and Ikaros (or functional portion thereof), e.g., the formation of a heterodimer.

In a specific embodiment, the cereblon-binding compound used in accordance with the methods described herein is pomalidomide (4-amino-2-[(3RS)-(2,6-dioxopiperidin-3-yl)-1H-isoindole-1,3(2H)-dione). In another specific embodiment, the cereblon-binding compound used in accordance with the methods described herein is thalidomide ((RS)-2-(2,6-dioxopiperidin-3-yl)-1H-isoindole-1,3(2H)-dione). In another specific embodiment, the cereblon-binding compound used in accordance with the methods described herein is lenalidomide (3-(4-amino-1-oxo-1,3-dihydro-2H-isoindol-2-yl)piperidine-2,6-dione). In another specific embodiment, the cereblon-binding compound used in accordance with the methods described herein is 3-[4-(4-morpholin-4-ylmethyl-benzyloxy)-1-oxo-1,3-dihydro-Isoindol-2-yl]-piperidine-2,6-dione. In another specific embodiment, the cereblon-binding compound used in accordance with the methods described herein is 3-(4-((4-((4-(2,4-difluorophenyl)piperazin-1-yl)methyl)benzyl)oxy)-1-oxoisoindolin-2-yl)piperidine-2,6-dione. See, e.g., U.S. Patent Application Publication No. 2014/0162282 for disclosure related to these compounds, which is incorporated by reference herein in its entirety.

A cereblon-binding compound used in accordance with the methods described herein, or an enantiomer or a mixture of enantiomers thereof; or a pharmaceutically acceptable salt, solvate, hydrate, co-crystal, clathrate, or polymorph thereof, can be delivered as a single dose such as, e.g., a single bolus injection, or oral tablets or pills; or over time, such as, e.g., continuous infusion over time or divided bolus doses over time.

The cereblon-binding compounds used in accordance with the methods described herein can be formulated for intravenous, intraarterial, parenteral, intramuscular, subcutaneous, intrathecal, or intraocular administration, or administration within a particular organ or tissue.

4.2. Artificial Cell Death Polypeptides 4.2.1. Cell Death Polypeptide Constructs Also provided herein is are dimerizable artificial cell death receptors comprising a first polypeptide comprising cereblon or a functional portion thereof and a second polypeptide comprising a cereblon-associated protein or a functional portion thereof that, when expressed in a cell, e.g., a T lymphocyte or NK cell, can lead to death of the cell in the presence of a cereblon-binding compound. Cereblon, cereblon-associated proteins, and cereblon-binding compound are described in detail in Section 4.1, above.

In a specific embodiment, provided herein is a dimerizable artificial cell death receptor comprising (a) a first polypeptide comprising an apoptosis-inducing domain (or functional portion thereof) and cereblon (or functional portion thereof) and (b) a second polypeptide comprising an apoptosis-inducing domain (or functional portion thereof) and Aiolos (or a functional portion thereof), wherein said cereblon (or functional portion thereof) and said Aiolos (or functional portion thereof) are both capable of binding a cereblon-binding compound, and wherein said first polypeptide and said second polypeptide dimerize in the presence of said cereblon-binding compound to generate an apoptosis-inducing signal. In a specific embodiment, said cereblon-binding compound is pomalidomide, thalidomide, lenalidomide, 3-[4-(4-morpholin-4-ylmethyl-benzyloxy)-1-oxo-1,3- dihydro-Isoindol-2-yl]-piperidine-2,6-dione, or 3-(4-((4-(2,4-difluorophenyl)piperazin-1-yl)methyl)benzyl)oxy)-1-oxoisoindolin-2-yl)piperidine-2,6-dione.

In another specific embodiment, provided herein is a dimerizable artificial cell death receptor comprising (a) a first polypeptide comprising a transmembrane protein that comprises a transmembrane domain and an intracellular domain comprising an apoptosis-inducing domain (or functional portion thereof) and cereblon (or functional portion thereof); and (b) a second polypeptide comprising an apoptosis-inducing domain (or functional portion thereof) and a cereblon-associated protein (or functional portion thereof). In a specific embodiment, said second polypeptide comprises a transmembrane protein comprising a transmembrane domain and an intracellular domain comprising an apoptosis-inducing domain (or functional portion thereof) and a cereblon-associated protein (or functional portion thereof). In a specific embodiment, said cereblon-associated protein is Aiolos or Ikaros.

In another specific embodiment, provided herein is a dimerizable artificial cell death receptor comprising (a) a first polypeptide comprising a transmembrane protein that comprises an extracellular domain comprising cereblon (or functional portion thereof), a transmembrane domain, and an intracellular domain comprising an apoptosis-inducing domain (or functional portion thereof); and (b) a second polypeptide comprising an apoptosis-inducing domain (or functional portion thereof) and a cereblon-associated protein (or functional portion thereof). In another specific embodiment, said second polypeptide comprises a transmembrane protein comprising a transmembrane domain and an intracellular domain comprising an apoptosis-inducing domain (or functional portion thereof) and a cereblon-associated protein (or functional portion thereof). In another specific embodiment, said second polypeptide comprises a transmembrane protein that comprises an extracellular domain comprising a cereblon-associated protein (or functional portion thereof), a transmembrane domain, and an intracellular domain comprising an apoptosis-inducing domain (or functional portion thereof). In a specific embodiment, the cereblon-associated protein is Aiolos or Ikaros.

In another specific embodiment, provided herein is a dimerizable artificial cell death receptor comprising (a) a first polypeptide comprising a transmembrane protein that comprises an apoptosis-inducing domain (or functional portion thereof) and cereblon (or functional portion thereof); and (b) a second polypeptide comprising a transmembrane protein that comprises a transmembrane domain and an intracellular domain comprising an apoptosis-inducing domain (or functional portion thereof) and a cereblon-associated protein (or functional portion thereof). In a specific embodiment, the cereblon-associated protein is Aiolos or Ikaros.

In another specific embodiment, provided herein is a dimerizable artificial cell death receptor comprising (a) a first polypeptide comprising a transmembrane protein that comprises an apoptosis-inducing domain (or functional portion thereof) and cereblon (or functional portion thereof); and (b) a second polypeptide comprising a transmembrane protein that comprises an extracellular domain comprising a cereblon-associated protein (or functional portion thereof), a transmembrane domain, and an intracellular domain comprising an apoptosis-inducing domain (or functional portion thereof). In a specific embodiment, the cereblon-associated protein is Aiolos or Ikaros.

The apoptosis-inducing domain of the cell death polypeptide can be, for example, any protein or portion thereof that when dimerized initiates an apoptosis-inducing signal in the cell. In certain embodiments, the apoptosis-inducing domain is any caspase that homodimerizes, In a specific embodiment, the apoptosis-inducing domain is or comprises a caspase, e.g., caspase 9, caspase 8, or caspase 3 (e.g., human caspase 9, caspase 8, or caspase 3). The amino acid sequences of human caspases, including human caspase 9, human caspase 8, and human caspase 3 are well known in the art. For example, human caspase 3 has been assigned NCBI Gene ID: 836; human caspase 8 has been assigned NCBI Gene ID: 841; and human caspase 9 has been assigned NCBI Gene ID: 842. In certain embodiments, the intracellular domain that is, or comprises, a caspase domain, and the extracellular domain, are joined by a CD8a stalk or CD80 stalk, at least part of which can function as a transmembrane domain.

4.2.2. Nucleic Acids

Provided herein are nucleic acids encoding the dimerizable artificial cell death receptors described herein, i.e., nucleic acids encoding the first polypeptide and nucleic acids encoding the second polypeptide of the dimerizable artificial cell death receptors described herein. In certain embodiments, a first polypeptide of a dimerizable artificial cell death receptors described herein is encoded by a first nucleic acid (polynucleotide) and the second polypeptide of a dimerizable artificial cell death receptors described herein is encoded by a second nucleic acid (polynucleotide). In a specific embodiment, provided herein is a nucleic acid (polynucleotide) that encodes both the first polypeptide and second polypeptide of a dimerizable artificial cell death receptor described herein.

Nucleic acids useful in the production of the artificial cell death receptors described herein include DNA, RNA, and nucleic acid analogs. Nucleic acid analogs can be modified at the base moiety, sugar moiety, or phosphate backbone, and can include deoxyuridine substitution for deoxythymidine, 5-methyl-2'-deoxycytidine or 5-bromo-2'-deoxycytidine substitution for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) Antisense Nucleic Acid Drug Dev. 7:187-195; and Hyrup et al. (1996) Bioorgan. Med. Chain. 4:5-23. In addition, the deoxyphosphate backbone can be replaced with, for example, a phosphorothioate or phosphorodithioate backbone, a phosphoroamidite, or an alkyl phosphotriester backbone.

In certain embodiments, the artificial cell death receptors-encoding nucleic acids described herein are comprised within a nucleic acid vector. For example, cells of interest, e.g., T lymphocytes, can be transformed using synthetic vectors, lentiviral or retroviral vectors, autonomously replicating plasmids, a virus (e.g., a retrovirus, lentivirus, adenovirus, or herpes virus), or the like, containing nucleic acid (polynucleotides) encoding the first and/or second polypeptides of the artificial cell death receptors described herein. In a specific embodiment, the vector comprising the first and/or second polypeptides of the artificial cell death receptors described herein is a retroviral vector. In another specific embodiment, the vector comprising the first and/or second polypeptides of the artificial cell death receptors described herein is a lentiviral vector. Lentiviral vectors suitable for transformation of cells, e.g., T lymphocytes, include, but are not limited to the lentiviral vectors described in U.S. Pat. Nos. 5,994,136; 6,165,782; 6,428,953; 7,083,981; and 7,250,299. HIV vectors suitable for transformation of cells, e.g., T lymphocytes, include, but are not limited to the vectors described in U.S. Pat. No. 5,665,577.

In certain embodiments, the artificial cell death receptor-encoding nucleic acids described herein are operably linked to a promoter. In a specific embodiment, said promoter is a T cell-specific promoter, a natural killer (NK) cell-specific promoter, an inducible promoter that functions within T cells or NK cells, or a constitutive promoter.

4.2.3. Cells

The artificial cell death receptors provided herein can be expressed in cells for which expression is useful, i.e., cells are engineered to comprise a artificial cell death receptor-encoding nucleic acid provided herein, such that, upon expression of the nucleic acid in the cell, the cell expresses an artificial cell death receptor described herein. For example, the artificial cell death receptors described herein can be expressed in T lymphocytes or natural killer cells. Cells provided herein that express the artificial cell death receptors described herein are referred to as "cell death receptor cells."

In a specific embodiment, the artificial cell death receptors provided herein are expressed in T lymphocytes. The T lymphocytes can be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T lymphocytes have been isolated from, or are expanded from T lymphocytes expanded from, peripheral blood, cord blood, or lymph.

In a specific embodiment, the cell death receptor cells described herein are autologous to an individual to whom the cells (e.g., T lymphocytes) are to be administered as part of a method of treatment described herein. In other embodiments, the cell death receptor cells described herein are allogeneic to an individual to whom the cells (e.g., T lymphocytes) are to be administered. Where allogeneic cells (e.g., T lymphocytes) are used to prepare cells comprising/expressing an artificial cell death receptor, it is preferable to select cells (e.g., T lymphocytes) that will reduce the possibility of graft-versus-host disease (GVHD) in the individual. See Section 4.1.

In one embodiment, T lymphocytes are obtained from an individual, optionally then expanded, and then transformed with a first vector encoding the first polypeptide of an artificial cell death receptor described herein and a second vector encoding the second polypeptide of an artificial cell death receptor described herein, and optionally then expanded. Double transformants may be selected using, e.g., a selectable marker unique to each of the vectors.

In another embodiment, T lymphocytes are obtained from an individual, optionally then expanded, and then transformed with a vector encoding the first polypeptide and the second polypeptide of an artificial cell death receptor described herein, and optionally then expanding. Cells containing the vector can be obtained using a selectable marker.

In certain embodiments, the T lymphocytes used to generate cell death receptor cells provided herein comprise native TCR proteins, e.g., TCR-α and TCR-β that are capable of forming native TCR complexes, in addition to an artificial costimulatory polypeptide (in embodiments in which a costimulatory polypeptide is used), or in addition to the first polypeptide and second polypeptide (in embodiments in which the cells comprise polypeptides separating the antigen binding signaling and costimulatory signaling). In certain other embodiments, either or both of the native genes encoding TCR-α and TCR-β in the T lymphocytes are modified to be non-functional, e.g., a portion or all are deleted or a mutation is inserted.

The cell death receptor cells provided herein, e.g., T cells or NK cells comprising a dimerizable artificial cell death receptor-encoding nucleic acid(s) described herein or expressing a dimerizable artificial cell death receptor described herein (i.e., expressing the first and second polypeptide of a dimerizable artificial cell death receptor described herein) can be induced to undergo apoptosis when contacted with a cereblon-binding compound, e.g., when contacted with pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

The cell death receptor cells provided herein can further be engineered to express a CAR, e.g., a CAR comprising a tumor-specific antigen binding domain. The CARs can be selected from, for example, first-generation CARs (in which the only signaling domain is CD3), second-generation CARs (which comprise signaling domains from CD3ζ and costimulatory domains from CD28), and third-generation CARs (which comprise signaling domains from CD3ζ and costimulatory domains from CD28 and another protein such as 4-1BB). In a specific embodiment, the CAR of the cell death receptor cells provided herein comprises two or more extracellular antigen-targeting domains. In another specific embodiment, said CAR of the cell death receptor cells provided herein comprises an extracellular domain that binds to an interleukin that is a negative regulator of T cell activity, and an intracellular domain from an interleukin receptor that is a positive regulator of T cell activity. In another specific embodiment, apoptosis is induced in a cell comprising an artificial cell death receptor and a CAR by contacting the cell with a cereblon-binding compound, e.g., pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

4.2.4. Methods of Use

The cells, e.g., T lymphocytes, provided herein that comprise an artificial cell death receptor provided herein and a CAR, can be used to treat an individual having one or more types of cells desired to be targeted by the cells described herein, e.g., one or more types of cells to be killed, wherein activity of the cell death receptor cells can be controlled by administration of a cereblon-binding compound. In particular, the cell death receptor cells can be used in treatment as a result of their CAR component, and can be killed when desired as a result of their cell death receptor component, wherein the killing is accomplished by contacting the cell death receptor cells with a cereblon-binding compound.

In a specific embodiment, provided herein is a method for controlled killing of target cells wherein said method comprises (i) contacting said target cells with a cell death receptor cell (e.g., a T cell or NK cell) comprising an artificial cell death receptor provided herein and a CAR and, when warranted, (ii) contacting said cell death receptor cell with a cereblon-binding compound, wherein in the presence of said cereblon-binding compound kills the cell death receptor cell, e.g., the cell death receptor cell undergoes apoptosis. In a specific embodiment, said target cell is a cancer cell, e.g., a blood cancer cell or a solid tumor cell. In another specific embodiment, said target cell expresses one or more the following antigens, or a fragment thereof: 4-1BB, 5T4, 8H9, B7-H6, adenocarcinoma antigen, α-fetoprotein, B Cell Maturation Antigen (BCMA), BAFF, B-lymphoma cell, C242 antigen, CA9, carcinoembryonic antigen, CA-125, carbonic anhydrase 9 (CA-IX), CCR4, CD3, CD4, CD19, CD20, CD22, CD23 (IgE receptor), CD28, CD30 (TNFRSF8), CD33, CD38, CD40, CD44v6, CD44v7/8, CD51, CD52, CD56, CD74, CD80, CD123, CD152, CD171, CD200, CD221, CE7, CEA, C-MET, CNT0888, CTLA-4, DRS, EpCAM, ErbB2, ErbB3/4, EGFR, EGFRvIII, EphA2, EGP2, EGP40, FAP, Fetal AchR, fibronectin extra domain-B, folate receptor-a, folate receptor 1, G250/CAIX, GD2, GD3, glycoprotein 75, GPNMB, HER2/neu, HGF, HLA-AI MAGE A1, HLA-A2 NY-ESO-1, HMW-MAA, human scatter factor receptor kinase, IGF-1 receptor, IGF-I, IgG1, IL-6, IL-13, IL-13 receptor a2, IL-11 receptor a, insulin-like growth factor I receptor, integrin a5I31, integrin avI33, Kappa light chain, L1-CAM, Lambda light chain, Lewis Y, mesothelin, MORAb-009, MS4A1, MUC1, MUC16, mucin CanAg, NCAM, N-glycolylneuraminic acid, NKG2D ligands, NPC-1C, PDGF-R a, PDL192, phosphatidylserine, prostate-specific cancer antigen (PSCA), prostatic carcinoma cells, PSMA, PSC1, RANKL, RON, ROR1, SCH 900105, SDC1, SLAMF7, sp17, TAG72, tenascin C, TGF β2, TGF-I3, TL1A, TRAIL-R1, TRAIL-R2, tumor antigen CTAA16.88, VEGF-A, VEGF receptors, VEGFR-1, VEGFR2, TEM1, TEM8, and/or vimentin.

In another specific embodiment, provided herein is a method of treating cancer, wherein said method comprises (i) administration of a population of cell death receptor cells (e.g., T cells or NK cells) comprising an artificial cell death receptor provided herein and a CAR, wherein said CAR comprises an antigen-binding domain specific for a cancer antigen (e.g., TSA or TAA) to a subject diagnosed with cancer (for example, a human subject) and, when warranted, (ii) contacting said cell death receptor cell with a cereblon-binding compound, wherein in the presence of said cereblon-binding compound the cell death receptor cell undergoes apoptosis. In a specific embodiment, said population of cells is administered first to the subject, followed by administration of the composition comprising a cereblon-binding compound at a specified period of time after administration of the cell population, e.g., 30 minutes, 1 hour, 6 hours, 12 hours, 1 day, 2 days, 3 days, 4 days, 5 days, 6 days, or 1 week after administration of the cell population. In another specific embodiment, said composition comprising a cereblon-binding compound is administered first to the subject, followed by administration of the said population of cells at a specified period of time after administration of the said composition comprising a cereblon-binding compound, e.g., 30 minutes, 1 hour, 6 hours, 12 hours, 1 day, 2 days, 3 days, 4 days, 5 days, 6 days, or 1 week after administration of the said composition comprising a cereblon-binding compound.

In a specific embodiment, said antigen bound by said CAR is 4-1BB, 5T4, 8H9, B7-H6, adenocarcinoma antigen, α-fetoprotein, B Cell Maturation Antigen (BCMA), BAFF, B-lymphoma cell, C242 antigen, CA9, carcinoembryonic antigen, CA-125, carbonic anhydrase 9 (CA-IX), CCR4, CD3, CD4, CD19, CD20, CD22, CD23 (IgE receptor), CD28, CD30 (TNFRSF8), CD33, CD38, CD40, CD44v6, CD44v7/8, CD51, CD52, CD56, CD74, CD80, CD123, CD152, CD171, CD200, CD221, CE7, CEA, C-MET, CNT0888, CTLA-4, DRS, EpCAM, ErbB2, ErbB3/4, EGFR, EGFRvIII, EphA2, EGP2, EGP40, FAP, Fetal AchR, fibronectin extra domain-B, folate receptor-a, folate receptor 1, G250/CAIX, GD2, GD3, glycoprotein 75, GPNMB, HER2/neu, HGF, HLA-AI MAGE A1, HLA-A2 NY-ESO-1, HMW-MAA, human scatter factor receptor kinase, IGF-1 receptor, IGF-I, IgG1, IL-6, IL-13, IL-13 receptor a2, IL-11 receptor a, insulin-like growth factor I receptor, integrin a5I31, integrin avI33, Kappa light chain, L1-CAM, Lambda light chain, Lewis Y, mesothelin, MORAb-009, MS4A1, MUC1, MUC16, mucin CanAg, NCAM, N-glycolylneuraminic acid, NKG2D ligands, NPC-1C, PDGF-R a, PDL192, phosphatidylserine, prostate-specific cancer antigen (PSCA), prostatic carcinoma cells, PSMA, PSC1, RANKL, RON, ROR1, SCH 900105, SDC1, SLAMF7, sp17, TAG72, tenascin C, TGF β2, TGF-I3, TL1A, TRAIL-R1, TRAIL-R2, tumor antigen CTAA16.88, VEGF-A, VEGF receptors, VEGFR-1, VEGFR2, TEM1, TEM8, and/or vimentin.

In a specific embodiment, the cereblon-binding compound administered to a subject in accordance with the methods of treating cancer described herein is pomalidomide, thalidomide, lenalidomide, 3-[4-(4-morpholin-4-ylmethyl-benzyloxy)-1-oxo-1,3-dihydro-Isoindol-2-yl]-piperidine-2,6-dione, or 3-(4-((4-((4-(2,4-difluorophenyl)piperazin-1-yl)methyl)benzyl)oxy)-1-oxoisoindolin-2-yl)piperidine-2,6-dione.

A non-limiting list of cancers that can be treated in accordance with the methods of treatment described herein includes lymphoma, leukemia, lung cancer, breast cancer, prostate cancer, adrenocortical carcinoma, thyroid carcinoma, nasopharyngeal carcinoma, melanoma, skin carcinoma, colorectal carcinoma, desmoid tumor, aesmoplastic small round cell tumor, endocrine tumor, Ewing sarcoma, peripheral primitive neuroectodermal tumor, solid germ cell tumor, hepatoblastoma, neuroblastoma, non-rhabdomyosarcoma soft tissue sarcoma, osteosarcoma, retinoblastoma, rhabdomyosarcoma, Wilms tumor, glioma, glioblastoma, myxoma, fibroma, and lipoma. Exemplary lymphomas and leukemias include, without limitation, chronic lymphocytic leukemia (small lymphocytic lymphoma), B-cell prolymphocytic leukemia, lymphoplasmacytic lymphoma, Waldenstrom macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma.

5. EXAMPLE

This Example describes the generation and use of modified T lymphocytes comprising a chimeric antigen receptor (CAR), wherein the CAR comprises a first polypeptide comprising an antigen binding domain specific to a tumor-specific antigen, a costimulatory domain, and cereblon, and second polypeptide comprising a cereblon-associated protein (e.g., Aiolos), and a CD3ζ immunoreceptor tyrosine-based activation motif (ITAM) primary cell signaling domain.

CAR Constructs

The CAR depicted in FIG. 1 is prepared using standard methodology.

A first polynucleotide encoding a first polypeptide, a tumor antigen binding protein (e.g., anti-HER2 scFv, anti-PSCA scFv or anti-BCMA scFv) cereblon (CRBN)-based CAR, i.e., "First Polypeptide," containing a scFv of an anti-tumor antigen antibody, a CD28 transmembrane (TM) domain, a CD28 costimulatory domain, and a CRBN is constructed. The first polynucleotide is cloned into a lentivirus vector.

A second polynucleotide encoding a second polypeptide, an Aiolos-based-ITAM CAR, i.e., "Second Polypeptide," containing a CD28 transmembrane (TM) domain, an Aiolos, and a CD3ζ ITAM domain is constructed. The second polynucleotide is cloned into a lentivirus vector.

Expression of CAR Constructs in T cells

The expression of the above-described CAR constructs by T cells is examined. To isolate T cells, peripheral blood mononuclear cells (PBMC) are separated from healthy donor blood (e.g., separating PBMC from whole blood-derived buffy coats using Ficoll-Paque Plus™ density gradient centrifugation (GE Healthcare, Piscataway, N.J.)). Pan T cells are negatively selected from PBMCs (e.g., by using the Pan T Isolation Kit II (Miltenyi Biotec, Cambridge, Mass.), according to the manufacturer's instructions).

Plasmids comprising the constructs encoding the First Polypeptide and Second Polypeptide CAR are introduced (e.g., by electroporation) into primary T cells, and the electroporated T cells are then cultured in media (e.g., RPMI-10) overnight. Expression of the antigen binding domain of the CAR is detected, confirming stable transfection of T cells by the construct encoding the First Polypeptide. For example, T cells are harvested at 24 hours post electroporation and stained to detect the antigen binding domain of the first polypeptide (e.g., for anti-HER2 detection, stained with HER2-human IgG-Fc chimera protein, followed by staining with an anti-human IgG-Fc antibody conjugated with APC). The stained cells are analyzed by flow cytometry. Stable transfection of T cells by the construct encoding the Second Polypeptide is confirmed. For example, the T cells are cultured in media (e.g., RPMI-10) supplemented with pomalidomide or lenalidomide overnight. T cells are harvested at 24 hours post electroporation and lysed followed by immunoprecipitation with an agent that can bind the antigen-binding domain of the First Polypeptide (e.g., for anti-HER2 detection, a HER2-human IgG-Fc chimera protein). Immunoprecipiates are treated with an agent that can detect and label the Aiolos or CD3 ζ domain of the Second Polypeptide (e.g., an anti-human Aiolos antibody or an anti-human CD3 ζ antibody). The labeled immunopreciptates are analyzed by ELISA and the Second Polypeptide is detected, confirming stable transfection of T cells by the construct encoding the Second Polypeptide.

Use of Pomalidomide or Lenalidomide to Regulate CAR T Cell Activity in Cancer Patients The First Polypeptide and Second Polypeptide CAR on a T cell is activated upon exposure to pomalidomide or lenalidomide and a tumor antigen. Pomalidomide and lenalidomide are well tolerated in humans.

Functional Evaluation of First and Second Polypeptide CARs

Functional evaluation of the First and Second Polypeptides in T-cells is performed (e.g., functional evaluation of a HER2-CAR; see below). T cells are stably transfected with the First and Second Polypeptides and stimulated with immobilized tumor-antigen-Fc chimera protein in the absence and presence of pomalidomide or lenalidomide. As a positive control for CD28 costimulation, another construct, which is identical to the CAR construct designated as the First Polypeptide, with the exception of the inclusion of a CD3ζITAM intracellular domain and exclusion of the cereblon, is generated. As negative controls, mock tranfections of the First Polypeptide (i.e., only the Second Polypeptide is transfected), the Second Polypeptide (i.e., only the First Polypeptide is transfected), and both First and Second Polypeptides (i.e., neither the First nor the Second Polypeptide is transfected) are performed.

To evaluate stimulation of the T cells, expression of the T cell activation markers CD69 and CD71 is examined 48 hours post-stimulation by flow cytometry and/or ELISA. Upregulation of CD69 and CD71 expression indicates stimulation of T cells. T cells that have been transfected with the constructs encoding the First and Second Polypeptides and constructs encoding postive and negative control polypeptides are tested for CD69 and CD71 expression. Upregulation of CD69 and CD71 expression in T cells transfected with the constructs encoding the First and Second Polypeptides relative to CD69 and CD71 expression observed in negative control cells indicates stimulation of the T cells transfected with constructs encoding the First and Second Polypeptides.

Treatment of Breast Cancer

An individual presents with stage 3 breast cancer that has spread to at least one regional lymph node. After surgery to remove cancerous tissue, the individual is administered between $10^9$ and $10^{10}$ modified T lymphocytes that comprise a First and Second Chimeric Receptors (such as the First and Second polypeptides described above), in 200 mL saline solution by intravenous infusion over 30 minutes. The first chimeric receptor comprises an extracellular antigen-binding region that binds to HER2, a transmembrane domain, an intracellular co-stimulatory domain from CD28, and a cereblon domain. The second chimeric receptor comprises a transmembrane domain, a cereblon-associated protein (e.g., an Aiolos), and a signal transfection domain derived from CD3 ζ.

The individual is administered pomalidomide or lenalidomide at a specified period of time after administration of the modified T lymphocytes that comprise the first and second chimeric receptor, e.g., 30 minutes, 1 hour, 6 hours, 12 hours, 1 day, 2 days, 3 days, 4 days, 5 days, 6 days, or 1 week after administration of the cell population.

Alternatively, the individual is administered pomalidomide or lenalidomide first, followed by administration of said modified T lymphocytes that comprise the first and second chimeric receptor at a specified period of time after administration of the pomalidomide or lenalidomide, e.g., 30 minutes, 1 hour, 6 hours, 12 hours, 1 day, 2 days, 3 days, 4 days, 5 days, 6 days, or 1 week after administration of the pomalidomide or lenalidomide.

The individual is assessed for breast cancer in remaining breast tissue, and spread to other lymph nodes, 30, 60, 90 and 180 days post-administration.

Treatment of Prostate Cancer

An individual presents with stage T2 prostate cancer, with no spread to regional or other lymph nodes (NO, MO).

Histological grade is determined to be G2. Overall, the individual is determined to have Stage II prostate cancer. The individual is administered between $10^9$ and $10^{10}$ modified T lymphocytes that comprise the First and Second Chimeric Receptors (such as the First and Second Polypeptides described above), in 200 mL saline solution by intravenous infusion over 30 minutes. The first chimeric receptor comprises an extracellular antigen-binding region that binds to PSCA, a transmembrane domain, intracellular co-stimulatory domains CD28, and a cereblon domain. The second chimeric receptor comprises a transmembrane domain, a cereblon-associated protein (e.g., an Aiolos), and a signal transfection domain derived from CD3ζ.

The individual is administered pomalidomide or lenalidomide at a specified period of time after administration of the modified T lymphocytes that comprise the First and Second Chimeric Receptor, e.g., 30 minutes, 1 hour, 6 hours, 12 hours, 1 day, 2 days, 3 days, 4 days, 5 days, 6 days, or 1 week after administration of the cell population.

Alternatively, the individual is administered pomalidomide or lenalidomide first, followed by administration of said modified T lymphocytes that comprise the First and Second Chimeric Receptor at a specified period of time after administration of the pomalidomide or lenalidomide, e.g., 30 minutes, 1 hour, 6 hours, 12 hours, 1 day, 2 days, 3 days, 4 days, 5 days, 6 days, or 1 week after administration of the pomalidomide or lenalidomide.

The individual is re-assessed for prostate cancer stage and spread to lymph nodes, and histology of biopsied prostate tissue is performed, at 30, 60 and 90 days post-administration.

Treatment of Multiple Myeloma

An individual presents with Stage III multiple myeloma (by the International Staging System or Durie-Salmon System) that has been previously treated with at least one course of therapy, e.g., lenalidomide or pomalidomide. The individual is administered between $10^8$ and $10^{10}$ modified T lymphocytes that comprise the First and Second Chimeric Receptors (such as the First and Second Polypeptides described above), in 200 mL saline solution by intravenous infusion over 30 minutes. The first chimeric receptor comprises an extracellular antigen-binding region that binds to BCMA, a transmembrane domain, intracellular co-stimulatory domains CD28, and a cereblon domain. The second chimeric receptor comprises a transmembrane domain, a cereblon-associated protein (e.g., an Aiolos), and a signal transduction domain derived from CD3ζ.

The individual is administered pomalidomide or lenalidomide at a specified period of time after administration of the modified T lymphocytes that comprise the First and Second chimeric receptor, e.g., 30 minutes, 1 hour, 6 hours, 12 hours, 1 day, 2 days, 3 days, 4 days, 5 days, 6 days, or 1 week after administration of the cell population.

Alternatively, the individual is administered pomalidomide or lenalidomide first, followed by administration of said modified T lymphocytes that comprise the first and second chimeric receptor at a specified period of time after administration of the pomalidomide or lenalidomide, e.g., 30 minutes, 1 hour, 6 hours, 12 hours, 1 day, 2 days, 3 days, 4 days, 5 days, 6 days, or 1 week after administration of the pomalidomide or lenalidomide.

The individual is re-assessed for multiple myeloma stage at 30, 60 and 90 days post-administration.

EQUIVALENTS

The present disclosure is not to be limited in scope by the specific embodiments described herein. Indeed, various modifications of the subject matter provided herein, in addition to those described, will become apparent to those skilled in the art from the foregoing description.

Such modifications are intended to fall within the scope of the appended claims.

Various publications, patents and patent applications are cited herein, the disclosures of which are incorporated by reference in their entireties.

What is claimed is:

1. A chimeric antigen receptor (CAR) comprising:
    (a) a first polypeptide comprising an antigen-binding domain; a transmembrane domain; cereblon or a functional portion thereof, wherein said cereblon or functional portion thereof is capable of binding to a cereblon-binding compound; and a primary cell signaling domain;
    wherein said first polypeptide does not comprise a costimulatory domain; and
    (b) a second polypeptide comprising a transmembrane domain; Aiolos or a functional portion thereof or Ikaros or a functional portion thereof, wherein said Aiolos or functional portion thereof or Ikaros or functional portion thereof is capable of binding the cereblon-binding compound; and a costimulatory domain;
    wherein in the presence of said cereblon-binding compound, said first polypeptide and said second polypeptide form a heterodimer.

2. The CAR of claim 1, wherein said first polypeptide comprises, in order from N-terminus to C-terminus: said antigen-binding domain, said transmembrane domain, said cereblon or functional portion thereof, and said primary cell signaling domain; and said second polypeptide comprises, in order from N-terminus to C-terminus: said transmembrane domain, said Aiolos or functional portion thereof or said Ikaros or functional portion thereof, and said costimulatory domain.

3. The CAR of claim 1, wherein said first polypeptide comprises, in order from N-terminus to C-terminus: said antigen-binding domain, said cereblon or functional portion thereof, said transmembrane domain, and said primary cell signaling domain; and said second polypeptide comprises, in order from N-terminus to C-terminus: said Aiolos or functional portion thereof or said Ikaros or functional portion thereof, said transmembrane domain, and said costimulatory domain.

4. The CAR of claim 1, wherein said primary cell signaling domain is CD3ζ.

5. The CAR of any of claims 1, wherein said signaling domain is or comprises an immunoreceptor tyrosine-based activation motif (ITAM).

6. The CAR of claim 5, wherein said ITAM is a signaling domain from one or more of FcRγ, FcRβ, CD3ζ, CD3γ, CD3δ, CD3ε, CD5, CD22, CD20, CD79a, CD79b, CD278 (ICOS), FcERI, CD66d, DAP10 and/or DAP12.

7. The CAR of any of claims 1, wherein said costimulatory domain comprises a functional signaling domain of one or more of CD28, 4-1BB (CD137), OX40, an activating NK cell receptor, BTLA, a Toll ligand receptor, CD2, CD7, CD27, CD30, CD40, CDS, ICAM-L LFA-1 (CD11a/CD18), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8α, CD8β, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, DAP10, DAP12, a ligand of CD83, an MHC class I molecule, a TNF receptor protein, an immunoglobulin-like protein, a cytokine receptor, an integrin, and/or a signaling lymphocytic activation molecule.

8. The CAR of any of claims 1, wherein said transmembrane domain is a transmembrane domain from alpha chain of the T-cell receptor, beta chain of the T-cell receptor, zeta chain of the T-cell receptor, CD28, CD3ε, CD45, CD4, CD5, CD8, CD9, CD16, CD22, CD33, CD37, CD64, CD80, CD86, CD134, CD137 or CD154.

9. The CAR of any of claims 1, wherein said antigen-binding domain is a receptor for said antigen.

10. The CAR of any of claims 1, wherein said antigen-binding domain is an antibody or binding fragment thereof that binds said antigen.

11. The CAR of claim 10, wherein said antibody or bingding fragment thereof is a single chain Fv fragment (scFv).

12. The CAR of any of claims 1, wherein said antigen is a tumor-associated antigen (TAA) or a tumor-specific antigen (TSA).

13. The CAR of claim 12, wherein said TAA or TSA is one or more of 4-1BB, 5T4, 8H9, B7-H6, adenocarcinoma antigen, α-fetoprotein, B Cell Maturation Antigen (BCMA), BAFF, B-lymphoma cell, C242 antigen, CA9, carcinoembryonic antigen, CA-125, carbonic anhydrase 9 (CA-IX), CCR4, CD3, CD4, CD19, CD20, CD22, CD23 (IgE receptor), CD28, CD30 (TNFRSF8), CD33, CD38, CD40, CD44v6, CD44v7/8, CD51, CD52, CD56, CD74, CD80, CD123, CD152, CD171, CD200, CD221, CE7, CEA, C-MET, CNT0888, CTLA-4, DRS, EpCAM, ErbB2, ErbB3/4, EGFR, EGFRvIII, EphA2, EGP2, EGP40, FAP, Fetal AchR, fibronectin extra domain-B, folate receptor-a, folate receptor 1, G250/CAIX, GD2, GD3, glycoprotein 75, GPNMB, HER2/neu, HGF, HLA-AI MAGE A1, HLA-A2 NY-ESO-1, HMW-MAA, human scatter factor receptor kinase, IGF-1 receptor, IGF-I, IgGl, IL-6, IL-13, IL-13 receptor a2, IL-11 receptor a, insulin-like growth factor I receptor, integrin a5I31, integrin avI33, Kappa light chain, L1-CAM, Lambda light chain, Lewis Y, mesothelin, MORAb-009, MS4A1, MUC1, MUC16, mucin CanAg, NCAM, N-glycolylneuraminic acid, NKG2D ligands, NPC-1C, PDGF-R a, PDL192, phosphatidylserine, prostate-specific cancer antigen (PSCA), prostatic carcinoma cells, PSMA, PSC1, RANKL, RON, ROR1, SCH 900105, SDC1, SLAMF7, sp17, TAG72, tenascin C, TGF β2, TGF-I3, TL1A, TRAIL-R1, TRAIL-R2, tumor antigen CTAA16.88, VEGF-A, VEGF receptors, VEGFR-1, VEGFR2, TEM1, TEM8, and/or vimentin.

14. The CAR of any of claims 1, wherein when said first polypeptide and said second polypeptide are expressed within a T cell or NK cell, and heterodimerize, the CAR transmits (i) a primary activation signal, or (ii) a primary activation signal and a costimulatory signal; wherein the primary activation signal or the primary activation signal and the costimulatory signal are capable of activating a T cell or NK cell.

15. The CAR of any of claims 1, wherein said cereblon-binding compound is thalidomide ((RS)-2-(2,6-dioxopiperidin-3-yl)-1H-isoindole-1,3(2H)-dione), lenalidomide (3-(4-amino-1-oxo-1,3-dihydro-2H-isoindol-2-yl)piperidine-2,6-dione), pomalidomide (4-amino-2-[(3RS)-(2,6-dioxopiperidin-3-yl)-1H-isoindole-1,3(2H)-dione), 3-[4-(4-morpholin-4-ylmethyl-benzyloxy)-1-oxo-1,3-dihydro-Isoindol-2-yl]-piperidine-2,6-dione; or 3-(4-((4-((4-(2,4-difluorophenyl)piperazin-1-yl)methyl)benzyl)oxy)-1-oxoisoindolin-2-yl)piperidine-2,6-dione.

16. The CAR of claim 2, wherein said antigen-binding domain is an antibody or binding fragment thereof that binds said antigen.

17. The CAR of claim 16, wherein said binding fragment is a single-chain antibody variable domain (scFv).

18. The CAR of claim 3, wherein said antigen-binding domain is an antibody or binding fragment thereof that binds said antigen.

19. The CAR of claim 18, wherein said binding fragment is a single-chain antibody variable domain (scFv).

20. The CAR of claim 1, wherein when said first polypeptide and said second polypeptide are expressed within a T cell or NK cell, and heterodimerize, the CAR transmits a primary activation signal and a costimulatory signal, wherein the primary activation signal and the costimulatory signal are capable of activating said T cell or NK cell.

21. The CAR of claim 1, wherein said costimulatory domain comprises a functional signaling domain of CD28 or 4-1BB (CD137).

22. The CAR of claim 4, wherein said costimulatory domain comprises a functional signaling domain of CD28 or 4-1BB (CD137).

\* \* \* \* \*

UNITED STATES PATENT AND TRADEMARK OFFICE
CERTIFICATE OF CORRECTION

PATENT NO. : 11,331,380 B2
APPLICATION NO. : 16/343375
DATED : May 17, 2022
INVENTOR(S) : Shuichan Xu It is certified that error appears in the above-identified patent and that said Letters Patent is hereby corrected as shown below:

In the Claims

In Claim 5 at Column 38, Line 48, please delete "any of claims" and substitute therefor:
--claim--.
In Claim 5 at Column 38, Line 48, please delete "said" and substitute therefor:
--said primary cell--.
In Claim 6 at Column 38, Line 54, please delete "and/or" and substitute therefor:
--and--.
In Claim 7 at Column 38, Line 55, please delete "any of claims" and substitute therefor:
--claim--.
In Claim 7 at Column 38, Line 57, please delete "of" and substitute therefor:
--of:--.
In Claim 7 at Column 38, Line 59, please delete "ICAM-L" and substitute therefor:
--ICAM-L,--.
In Claim 7 at Column 38, Line 65, please delete "CD11a, LFA-1," and substitute therefor:
--CD11a,--.
In Claim 7 at Column 39, Line 9, please delete "and/or" and substitute therefor:
--and--.
In Claim 8 at Column 39, Line 11, please delete "any of claims" and substitute therefor:
--claim--.
In Claim 8 at Column 39, Line 12, please delete "from" and substitute therefor:
--from:--.
In Claim 9 at Column 39, Line 17, please delete "any of claims" and substitute therefor:
--claim--.
In Claim 10 at Column 39, Line 19, please delete "any of claims" and substitute therefor:
--claim--.
In Claim 11 at Column 39, Line 23, please delete "bingding" and substitute therefor:
--binding--.
In Claim 12 at Column 39, Line 25, please delete "any of claims" and substitute therefor:
--claim--.

Signed and Sealed this
Seventh Day of February, 2023

Katherine Kelly Vidal
*Director of the United States Patent and Trademark Office*

In Claim 13 at Column 40, Line 7, please delete "and/or" and substitute therefor:
--and--.
In Claim 14 at Column 40, Line 8, please delete "any of claims" and substitute therefor:
--claim--.
In Claim 14 at Column 40, Line 11, please delete "signal," and substitute therefor:
--signal--.
In Claim 14 at Column 40, Line 14, please delete "a" and substitute therefor:
--said--.
In Claim 15 at Column 40, Line 16, please delete "any of claims" and substitute therefor:
--claim--.